(12) United States Patent
Freed

(10) Patent No.: US 8,206,993 B2
(45) Date of Patent: *Jun. 26, 2012

(54) METHOD FOR DETERMINING THE CHARACTERISTICS OF CRUDE OILS AND MIXTURES OF CHAIN MOLECULES BY DIFFUSION, RELAXATION AND DENSITY MEASUREMENTS

(75) Inventor: Denise Freed, Newton Highlands, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/749,216

(22) Filed: Mar. 29, 2010

(65) Prior Publication Data

US 2010/0236326 A1 Sep. 23, 2010

Related U.S. Application Data

(62) Division of application No. 10/864,124, filed on Jun. 9, 2004, now Pat. No. 7,718,434.

(51) Int. Cl.
*G01N 24/00* (2006.01)
(52) U.S. Cl. ............... 436/173; 436/28; 436/29; 436/85
(58) Field of Classification Search .................... None
See application file for complete search history.

(56) References Cited

OTHER PUBLICATIONS

Yoo et al. "Viscosity and Diffusion of Small Normal and Isomeric Alkanes: An Equilibrium Molecular Dynamics Simulation Study", Bull. Korean Chem. Soc., 2008, vol. 29, No. 5, pp. 1059-1062.*

* cited by examiner

*Primary Examiner* — Yelena G Gakh

(57) ABSTRACT

The diffusion coefficients and relaxation times of mixtures of alkanes follow simple scaling laws based on the chain length of the constituents and the mean chain length of the mixture. These scaling laws are used to determine chain sizes in a mixture from the distribution of the diffusion coefficients. These scaling laws can be used to determine the mean chain lengths (or chain lengths) of a sample (alkanes or mixtures of alkanes) and therefore the constituents of the sample.

26 Claims, 15 Drawing Sheets

METHOD FOR DETERMINING THE CHARACTERISTICS OF CRUDE OILS AND MIXTURES OF CHAIN MOLECULES BY DIFFUSION, RELAXATION AND DENSITY MEASUREMENTS

The present invention is a divisional filing of U.S. patent application Ser. No. 10/864,124, filed Jun. 9, 2004, now U.S. Pat. No. 7,718,434.

FIELD OF THE INVENTION

The present invention relates to a method of modeling alkanes and, more particularly, to a method of determining the constituents of an oil mixture and its viscosity.

BACKGROUND OF THE INVENTION

It is well known that the self-diffusion coefficient of a molecule is related in some way to its size. For a hard sphere in a fluid with viscosity $\eta_s$, the relationship is given by the Einstein-Stokes equation, $$D = \frac{k_B T}{6\pi \eta_s r} \qquad (1)$$

where r is the radius of the sphere and $\eta_s$ is the viscosity of the solvent. This equation suggests that in a mixture with molecules of different radii, the diffusion coefficient $D_i$ of the $i^{th}$ component is $$D_i = \frac{k_B T}{6\pi \eta_s r_i} \qquad (2)$$

where $r_i$ is the radius of the $i^{th}$ component. From this, it can be concluded that the ratio of the diffusion coefficients of any two components in the mixture will depend only on the ratios of the sizes of the two molecules and is independent of any other properties of the fluid, such as its viscosity or temperature. Alternatively, Equation (2) implies that for a particular mixture, $D_i r_i$ is constant for all components in the mixture. In addition, Equation (2) states that there is a fixed relationship between the diffusion coefficients and the viscosity of the fluid ($D \propto 1/\eta_s$).

An application of the hard sphere model to oils may be found in Freedman et al. "A New NMR Method of Fluid Characterization in Reservoir Rocks: Experimental Confirmation and Simulation Results," paper SPE 63214 presented at the 2000 SPE Annual Technical Conference and Exhibition, Dallas, 1-4 October; Lo et al. "Relaxation Time and Diffusion Measurements of Methane and Decane Mixtures," The Log Analyst (November-December 1998); and Lo et al. "Correlations of NMR Relaxation Time with Viscosity, Diffusivity, and Gas/Oil Ratio of Methane/Hydrocarbon Mixtures," in Proceedings of the 2000 Annual Technical Conference and Exhibition, Society of Petroleum Engineers (October 2000). These articles are hereby incorporated by reference herein in their entireties.

As shown in FIG. 1, diffusion coefficient D is related to the size of the molecule. Diffusion depends on the constituents (components and relative amounts) of the mixture under analysis. However, existing models do not adequately describe the physics of the system sufficient to identify the components of the mixture to an acceptable degree of certainty.

However, the hard sphere model is not adequate for describing more complicated molecules, such as oils, which are floppy chains. One example of the failure of the hard sphere model is evidenced by the measurements of diffusion and viscosity in alkanes and oils. In plots of log D versus log $kT/\eta$ (see FIG. 2), the data all lie on a single line, regardless of the molecule's radii. These plots are in disagreement with Equation (2), which would imply that the slope depends on the radius of the molecule.

As will be shown below, elevated temperature and pressure may influence the modeling of complicated oils. Applications of the hard sphere model to oils do not adequately account for the effects of temperature and pressure on the diffusion coefficients and relaxation times.

Accordingly, it is one object of the present invention to provide a method to more appropriately model oils and oil mixtures.

It is another object of the present invention to provide a model that accounts for the temperature and pressure dependence of the diffusion coefficient and relaxation times over a wide range of temperatures and pressures.

SUMMARY OF THE INVENTION

Accordingly, the present inventor has discovered that diffusion coefficients and relaxation times of mixtures of alkanes follow simple scaling laws based on the chain length of the constituents and the mean chain length of the mixture. These scaling laws are used to determine chain sizes in a mixture from the distribution of the diffusion coefficients. These scaling laws can be used to determine the mean chain lengths (or chain lengths) in live oils as well as the viscosity of a mixture.

It is noted the use of scaling laws have not been used to give a complete description for mixtures of short chain molecules, crude oils, or the like. As is commonly known in prior art, scaling laws generally refer to power laws, where one quantity, x, is equal to another quantity, y, raised to some power v, so that $x=ay^v$. Although v is sometimes determined a priori, often v and the constant of proportionality, a, must be determined for the specific properties and conditions of interest. Scaling laws generally describe very large systems, such as very long chains, and in prior art are not usually expected to be valid for short chains.

In addition, the present invention characterizes the relationship between diffusion coefficients $D_i$ or nuclear magnetic relaxation times $T_{1i}$ and $T_{2i}$ and molecular composition for mixtures of alkanes at elevated pressures and temperatures. Using properties of the free volume theory and the behavior of the density of alkanes, for a large range of pressures, the diffusion coefficients and relaxation times depend on pressure and mean chain length of the mixture only through the density. Accordingly, a method is provided for determining the relationship between $D_i$, $T_{1i}$ or $T_{2i}$ and composition at elevated pressures, as long as the density of the fluid is known. In addition, the relationship between $D_i$, $T_{1i}$ or $T_{2i}$ and composition can be determined at arbitrary pressure P as long as it is known at a suitable reference pressure $P_0$. The scaling laws for $D_i$, $T_{1i}$ and $T_{2i}$ and the Ahrrenius dependence on temperature are combined to obtain the temperature dependence of the diffusion coefficient and relaxation times. Once the relationship between $D_i$, $T_{1i}$ or $T_{2i}$ and composition is known, measurements of the diffusion coefficients and relaxation times, using various nuclear magnetic resonance (NMR) tools such as Schlumberger's MRX™, can be used to obtain the composition of mixtures of alkanes. In addition, this technique may be applied to diffusion and relaxation data collected from fluid sampling tools and may be practiced in the field (i.e. downhole) or in a laboratory. In addition diffusion-edited data such as that collected using the techniques of commonly owned U.S. Pat. No. 6,570,382 may be evaluated using this method. It is further noted that this technique may be applied to non-NMR diffusion data as may be known in the art. It is further noted that diffusion measurements may be preferred over relaxation measurements, particularly for small chain lengths (i.e., methane and ethane) where additional physics come into play.

Accordingly, expressions for diffusion coefficient and relaxation times may be determined as a function of chain lengths at elevated pressures and temperatures using: (1) density data for pure alkanes at the desired pressures and temperatures and (2) data on diffusion coefficients or relaxation times for pure or mixed alkanes at one reference pressure and several temperatures. Preferably, this data spans the range of chain lengths or densities of interest. Once the relation between D, $T_1$, or $T_2$ and chain lengths is known, it can be used with the modeling methods herein to determine chain length distributions from diffusion or relaxation measurements.

This method is applicable for a wide range of temperatures and pressures and for chain lengths less than the entanglement length. For pressures above about 100 MPa careful selection of the reference pressure is recommended. It is also noted that for pressures above about 100 MPa the slope of the calibration curve may begin to change and should be accounted for. If asphaltenes or a large amount of aromatics are expected to be present, it may be preferable to obtain one or more additional measurements to determine the type of molecules in the mixtures. A difference between the chain length distribution found by measuring the distributions of diffusion coefficients and relaxation times may identify the presence of asphaltenes. Asphaltenes form large aggregates that tumble slowly, $T_2$ is sensitive to this slow motion while $T_1$ is not sensitive to this motion. This leads to a shortening of $T_2$ as compared to $T_1$. This difference between $T_1$ and $T_2$ can be used to identify the presence of asphaltenes.

The method of the present invention can be quite useful in detecting gradients in composition along a well or between wells. If the oil is of the type that varies with temperature and pressure as in the alkane model, then the NMR derived distribution could be calibrated with laboratory oil measurements at a few places, and points between the measured NMR distributions would indicate composition gradients. In the absence of lab measurements, the NMR distributions can show composition gradients; however, lab measurements would verify that the temperature and pressure dependence is of the expected form.

One advantage of obtaining the composition from the diffusion or relaxation measurements is that it is complementary to optical measurements, first, because they measure different types of physics, and second, because they NMR measurement can give some detailed information about the molecules with longer chain lengths, while optical measurements can give details about the exact methane content and the presence of other gases. Methane can affect the scaling law for the NMR relaxation times, while the presence of other gases such as $CO_2$ and nitrogen can affect the density, diffusion, and relaxation. It may be useful to know how much of these gases are present to properly invert the $T_1$ and diffusion data for the chain length distributions. On the other hand, the presence of the large molecules, which is given by the NMR measurements, can greatly affect the properties of the oil, such as whether it can become waxy.

Because the NMR measurements are sensitive to larger particles, it can also be useful for detecting phase changes. As waxes or asphaltenes start to aggregate or precipitate, they should appear in the chain length distribution as much larger particles, which can signal a phase change as the temperature or pressure is changed.

Accordingly, the present invention provides a method of determining the constituents of an oil mixture and its viscosity. The method of the present invention includes using commonly known nuclear magnetic resonance techniques to determine the diffusion distribution of a mixture and, using polymer models, correlating this diffusion distribution to chain length of the constituents, the mean chain length of the mixture, or its viscosity.

Accordingly, a first embodiment of the present invention is a method for determining the characteristics of a fluid sample, comprising: (a) obtaining measurements (diffusion or relaxation measurements) on a plurality of calibration samples having one or more known constituents; and (b) determining the scaling law of said plurality of fluid samples using as a function of chain length said measurements of (a). To create an accurate calibration, the calibration samples should have a variety of mean chain lengths. In addition, the calibration samples may be pure alkanes or mixtures of alkanes, or a combination thereof. Once this calibration is determined, the constituents of a sample under investigation may be determined by obtaining either diffusion measurements and relaxation measurements, depending on the measurements made in (a) above and then applying the scaling law of (b) to these measurements. It is noted that the calibration does not need to be redone for each sample; once a calibration is performed, it may be reused for other samples. In one application of this embodiment, the calibration measurements and the sample measurements are performed at a first temperature and a reference pressure. The scaling law may be obtained by performing a two-parameter fit of the function, such as by identifying the slope and intercept of the scaling law. It is preferable to perform the calibration at the temperature and pressure approximately equal to the expected temperature and a second pressure. This method allows the determination of the mean chain length and the distribution of chain lengths of the constituents of the sample under investigation. From this information, the composition of the sample may be determined.

In a second embodiment, a method for determining the characteristics of a fluid sample is disclosed, wherein the calibration samples are subject to different temperatures and the reference pressure. In this case the scaling law becomes a function of mean chain length and temperature and it is no longer necessary to substantially match the temperature of the calibration samples to the expected temperature of the sample under investigation. Now the scaling law may be determined using a four parameter fit, as described in more detail below.

In a third embodiment, a method for determining the characteristics of a fluid sample is disclosed, comprising: (a) obtaining measurements (diffusion or relaxation measurements) of a plurality of calibration samples at a first temperature and a reference pressure, wherein the calibration samples have differing mean chain lengths; (b) determining the density of more than one pure alkane or mixtures of alkanes (not necessarily the same as the calibration samples) at the first temperature and the reference pressure, wherein density is determined as a function of mean chain length; (c) obtaining measurements (diffusion or relaxation measurements) of the sample under investigation at the first temperature and a second pressure; (d) determining the density of the sample under investigation at the first temperature and the second pressure; (e) applying the density function of (c) to the density measurements of (d) and using the measurements of (a) to determine the scaling law at the second pressure in terms of chain length; (f) applying the scaling law of (e) to the data of (c) to determine the composition of the sample under investigation. The density measurements of (b) may be obtained from standard look-up tables (such as the NIST webbook). This method can be used to determine the composition of the sample under investigation by determining the distribution of chain lengths of the constituents of the sample under investigation. It is noted that the density measurements of (b) can be any density, including, but not limited to, mass density, carbon density, and hydrogen density (more commonly known as the hydrogen index).

The fourth embodiment comprises a manipulation of the third embodiment, wherein a range of temperatures is accounted for. More specifically, a method for determining the characteristics of a fluid sample is disclosed, comprising: (a) obtaining measurements (diffusion or relaxation measurements) of a plurality of calibration samples at reference pressure and at more than one temperature, wherein the calibration samples have differing mean chain lengths; (b) determining the density of more than one pure alkane or mixtures of alkanes at the reference pressure and at a temperature within or near the range of temperatures in (a), wherein density is determined as a function of mean chain length; (c) obtaining measurements (diffusion or relaxation measurements) of the sample under investigation at a second pressure and at a temperature within or near the range of temperatures in (a); (c) determining the density of the sample under investigation at the second pressure and at a temperature within or near the range of temperatures in (a); (d) applying the density function of (c) to the density measurements of (d) and using the measurements of (a) to determine the scaling law at the second pressure in terms of chain length; (e) applying the scaling law of (e) to the data of (c) to determine the composition of the sample under investigation.

In a fifth embodiment, a method for determining the characteristics of a fluid sample is disclosed, comprising: (a) obtaining measurements (diffusion or relaxation measurements) of a plurality of calibration samples at a first temperature and a reference pressure, wherein the calibration samples have differing mean chain lengths; (b) obtaining measurements (diffusion or relaxation measurements) of a sample under investigation at the first temperature and at a second pressure; (c) determining the relationship of volume of one or more alkanes or mixtures of alkanes (not necessarily the calibration sample) to (i) the mean chain length at the first temperature and the reference pressure and (ii) the mean chain length at the first temperature and a second pressure; (d) determining the scaling law as a function of chain length, using the functions of (c) and the measurements of (a); (e) applying the scaling law of (d) with the measurements of (b) to determine the composition of the sample under investigation. The volumes of (c) may be obtained using standard look-up tables (such as the NIST webbook). Further, the volumes may be any volume, including, but not limited to, volume per mole (molar volume), volume per hydrogen atom, or volume per carbon atom.

The sixth embodiment is a manipulation of the fifth embodiment to account for various temperatures. More specifically, a method for determining the characteristics of a fluid sample, comprising: (a) obtaining measurements (diffusion or relaxation measurements) of a plurality of calibration samples at more than one temperature and a reference pressure, wherein the calibration samples have differing mean chain lengths; (b) obtaining measurements (diffusion or relaxation measurements) of a sample under investigation at a temperature within or near the range of temperatures of the measurements of (a) and at a second pressure; (c) determining the relationship of volume of alkanes or mixtures of alkanes to (i) the mean chain length at the reference pressure and (ii) the mean chain length at the second pressure; (d) determining the scaling law in terms chain length and temperature at the second pressure using the functions of (c) and the measurements of (a); (e) applying the scaling law of (d) with the measurements of (b) to determine the composition of the sample under investigation.

It is envisioned that these methods may be performed in a laboratory or at the point of sampling. For example, these methods may be particularly useful in the characterization of oilfields and may be used on samples obtained from the earth formation or within the earth formation.

Further features and applications of the present invention will become more readily apparent from the figures and detailed description that follows.

DETAILED DESCRIPTION OF THE INVENTION

Modeling Oils

Figure 2:
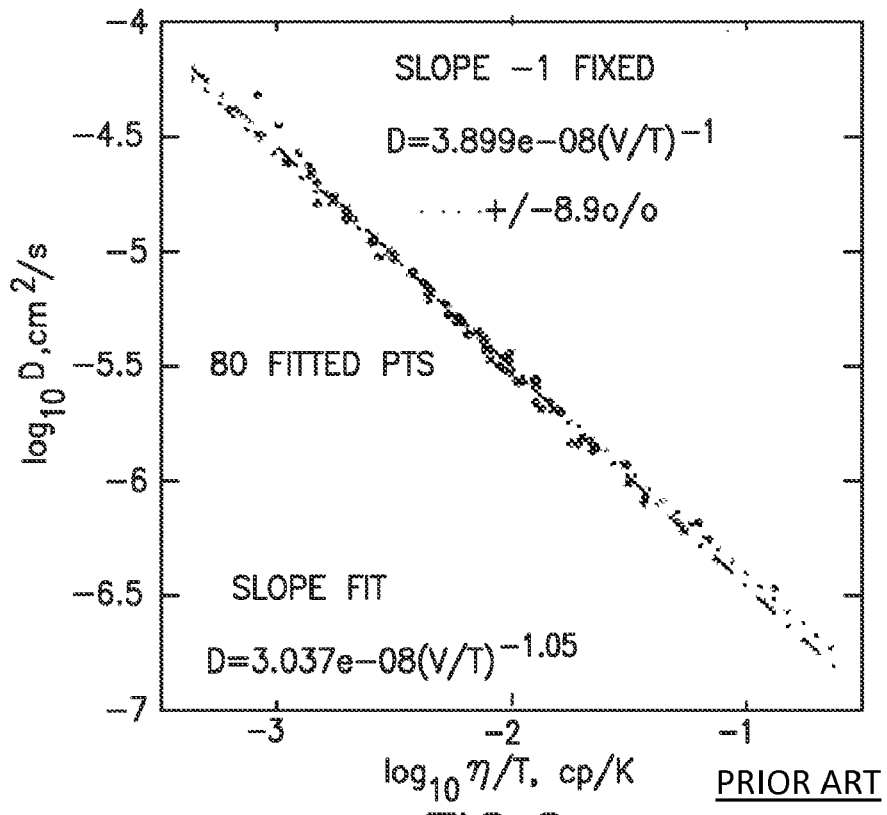
FIG. 2 is a graph showing the relationship between log D and log η/T to test the hard sphere model.

Properties that follow from Equation (2) suggest a method for fluid typing using diffusion data of oils. The ratio of diffusion coefficients within a given mixture gives the ratio of the "sizes" of the components. Furthermore, if it is known how the product $D_i r_i$ depends on the particular mixture, then the actual sizes of the molecules may be recovered, not just their ratios. As will be discussed below, polymer physics concepts may be used to show how diffusion data from mixtures of alkanes and live alkanes can be used to recover information about the chain lengths within a mixture as well as information about the mean chain length. The polymer model can also be used to explain the relationship between diffusion and viscosity as shown in FIG. 2.

Figure 3:
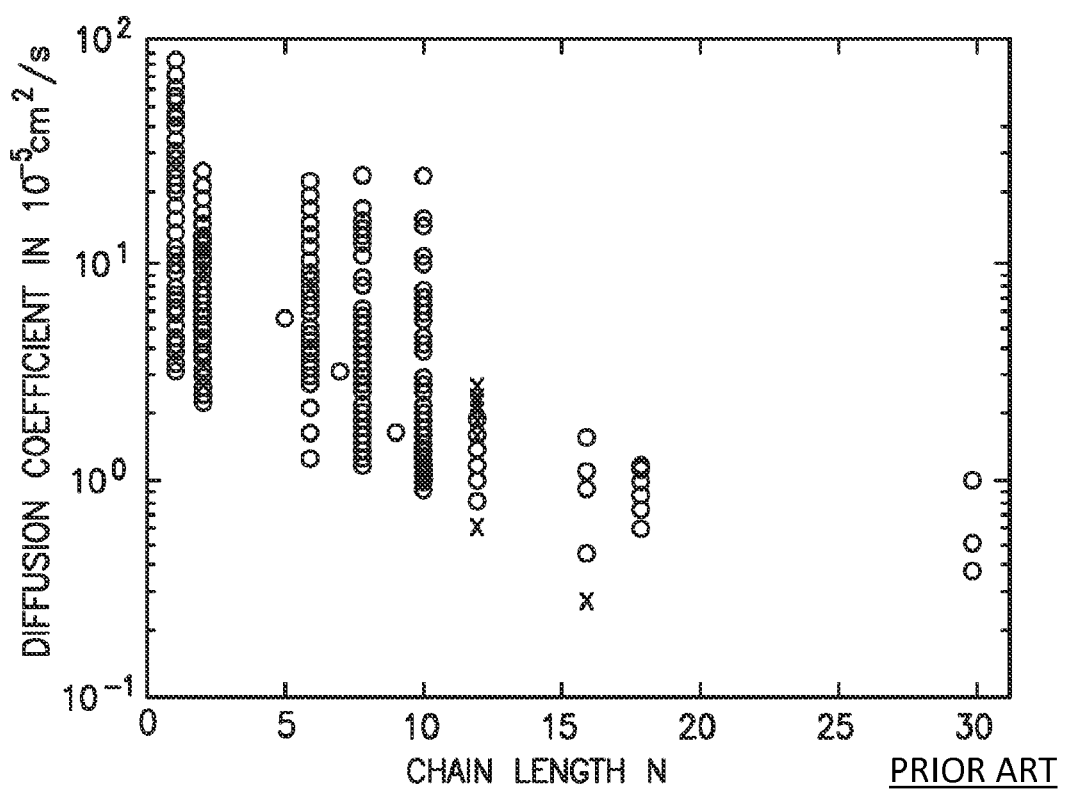
FIG. 3 is a graph showing the relationship between diffusion coefficient and chain length for pure alkanes and mixtures.

FIG. 3 shows that as a function of chain length, the diffusion coefficient can vary greatly. This graph is based on data collected from numerous sources, including Dymond et al. "The Temperature and Density Dependence of the Self-Diffusion Coefficient of n-hexadecane," Molec. Phys. 75(2):461-466 (1992) and Marbach et al. "Self- and Mutual Diffusion Coefficients of some n-Alkanes at Elevated Temperature and Pressures," Z. Phys. Chem., Bd. 193, S:19-40 (1996) (incorporated by reference herein in their entireties). The data shown is measured at differing temperatures and pressures for differing mixtures. Accordingly, diffusion coefficients also vary as a function of temperature, pressure, and constituents of the mixture. Thus, an improved model for diffusion in mixtures is required, if one is able to use the diffusion coefficients to invert for chain lengths. As shown below, the ratio of diffusion coefficients in a mixture depends only on the relative size of the molecules in the mixture and the internal viscosity depends only on the mean chain length of the mixture.

An aspect of this invention is to show how polymer models may be used to describe mixtures of alkanes. Doi et al. *The Theory of Polymer Dynamics*, Oxford University Press, New York (1996) and Ferry, *Viscoelastic Properties of Polymers*, John Wiley & Sons, Inc., New York (1980) (incorporated by reference herein in their entireties) provides a complete description of the polymer models. In the polymer models, the molecule is modeled by a chain of beads with a gaussian distribution of bond lengths between adjacent beads, which leads to a spring-like interaction between adjacent beads (also referred to as a "gaussian chain"). Each bead is subject to a Brownian force which is due to (1) the solvent molecules if the polymer is in a solvent and (2) the beads of the other polymers if the polymer is in a melt. For long chains (roughly 100 beads or longer), this model is a good description, provided an effective distance between adjacent beads, l, is assigned that is not always equal to the actual distance between the beads. In that case, the mean radius of gyration of the chain is given by $$R_g = \frac{N^D l}{\sqrt{6}} \quad (3)$$

where N is the chain length. For alkanes, N is equal to the number of carbon atoms. The exponent ν is approximately equal to ½ if there are no excluded volume effects and ⅗ if there are excluded volume effects.

For alkanes found in oils, the chain lengths are usually too short to be perfectly described by the ideal gaussian chain, because the chains are stiffer than a true gaussian chain. For very long alkanes and polymethylene chains (with N≧100) where gaussian behavior is observed, the parameter l is about $\sqrt{6.7}$ times the actual distance between carbon atoms. For shorter chains, l is not a constant. Instead, it varies with chain length, decreasing to the actual distance between carbon atoms for a chain length of two. However, even when other types of interactions between beads are used, many of the results for gaussian chains still apply, at least qualitatively.

Figure 4:
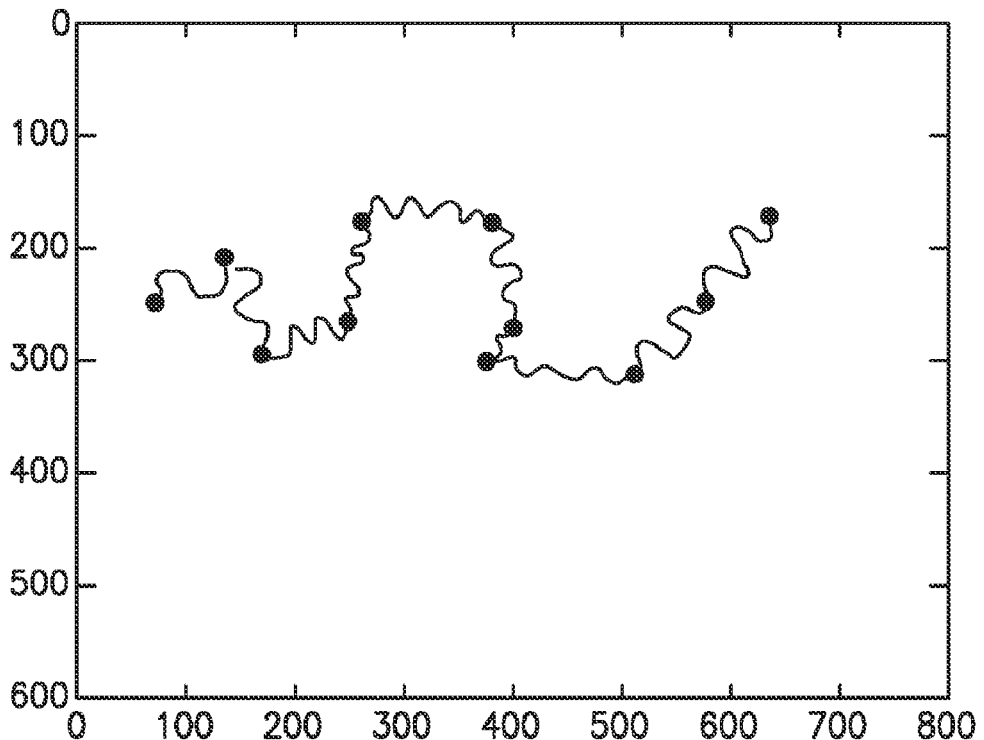
FIG. 4 illustrates the Rouse model.

Oils and liquid alkanes are melts. In melts, it is usually assumed that the hydrodynamic effects are screened out by the chains and that the excluded volume effects within a chain are balanced out by the excluded volume effects between differing chains. In that case, the melt is described by the Rouse model (shown in FIG. 4), which is the simplest version of the polymer models (see Rouse, J. Chem. Phys. 21:1272 (1953) (incorporated by reference herein in its entirety)). In the Rouse model, the translational diffusion coefficient of the molecule is given by $$D = \frac{k_B T}{N \xi} \quad (4)$$

where ξ is the friction constant for a bead and N is the number of beads in the chain. The Rouse model accounts for the gaussian interaction between nearest neighbors and each bead feeling the coefficient of friction, ξ, from the surrounding fluid.

For the shorter chains such as the alkanes, the hydrodynamic effects are not necessarily all screened out. The Zimm model adds the hydrodynamic effects to the Rouse model (see Zimm, J. Chem. Phys. 24:269 (1956) (incorporated by reference herein in its entirety)). In the Zimm model, the translational diffusion coefficient is given by $$D \approx 0.2 \frac{k_B T}{\eta_s \sqrt{6} R_g} \quad (5)$$

and, in the absence of excluded volume effects, the rotational diffusion coefficient is given by $$D_R = \frac{\sqrt{(3\pi)} k_B T}{\eta_s (\sqrt{6} R_g)^3} \quad (6)$$

where the radius of gyration is given by Equation (3). The viscosity $\eta_s$ is the viscosity that each bead sees. For example, if the polymer is dissolved in a solvent, it is the viscosity of the solvent. In the melt, it may be considered as the "internal viscosity" that each bead sees due to the high frequency motion of all the beads on the other chains in the melt. Equations (5) and (6) have a form very similar to the diffusion coefficients for the hard sphere model, but now the radius of the molecule scales with chain length as a function of $N^{1/3}$ (as compared to Equation (3) where the radius scales with chain length $N^\nu$), and the internal viscosity $\eta_s$ is not necessarily equal to the macroscopic viscosity of the fluid.

Even though the chains encountered in most oils are short and therefore are not perfect gaussian chains, many ideas about the collective motion of the internal degrees of freedom inherent in polymer models still apply. As discussed below, many of the polymer results appear to apply to the alkanes, at least qualitatively, if not quantitatively. Accordingly, the chains follow similar scaling laws.

Based on the polymer models, it is expected that the diffusion coefficient of the $i^{th}$ component of an alkane in a mixture is $$D_i = \frac{ak_B T}{N_i^\nu \eta_0} \quad (7)$$

where $N_i$ is the chain length or number of carbon atoms of the alkane; $\eta_0$ is the internal viscosity or coefficient of friction associated with the motion of a single bead; and a is a constant that depends on which model is appropriate for describing the fluid.

According to the various polymer models, it is expected that $0.5 \leq \nu \leq 1$. In the example presented herein, $\nu \approx 0.7$ (see the fit of the data in FIG. 5), in contrast to the value of $\nu=1$ which is usually assumed for polymer and alkane melts. The lower value of $\nu$ probably reflects the fact that the hydrodynamic effects are not fully screened in the alkane melts and that excluded volume effects or the stiffness of the chains play a role. It is still expected that for very long chains (but before the onset of entanglements) the value of $\nu$ will approach the ideal value of 1.

The methane and ethane molecules (and, most likely, the alkanes up to and including pentane) are more appropriately described by the hard sphere model, so it is expected that their diffusion coefficients will have the form $$D_i = \frac{ak_B T}{r_i \eta_0} \quad (8)$$

where $r_i$ is related to the radius of the molecule. In this equation, the same constant a and internal viscosity $\eta_0$ is used as in Equation (7). This means that $r_i$ is unitless and thus can be compared with the value of $N_i^\nu$ appropriate for the longer chains. Thus, one aspect of this invention is treating the oil and dissolved gas in a similar manner so that for both the oil and the gas the diffusion equation can be given by Equation (8). Fitting to the data for binary mixtures with ethane and methane in Helbaek et al., "Self-Diffusion Coefficients of Methane or Ethane Mixtures with Hydrocarbons at High Pressure by NMR," J. Chem. Eng. Data 41:598-603 (1996) (incorporated by reference herein in its entirety) gives, for methane $$r_m \approx 1.64 \quad (9)$$

and for ethane $$r_e \approx 2.32 \quad (10)$$

Within a mixture, then, the ratio of the diffusion coefficients of any two components depends on the ratio of their radius or chain length to some power. In other words, if components 1 and 2 are oils, then their diffusion coefficients have the ratio $$D_1/D_2 = N_2^\nu/N_1^\nu \quad (11)$$

regardless of any other properties of the mixture, such as its composition, temperature or pressure. Similarly, for a gas and an oil, the ratio would be $$D_g/D_o = N_o^\nu/r_g \quad (12)$$

These equations are similar to what one would expect reading Bearman, "Statistical Mechanical Theory of Diffusion Coefficients in Binary Liquid Solutions," J. Chem. Phys. 32(5):1308-1313 (1959) (incorporated by reference herein in its entirety) for nearly ideal fluids where the molar volume of the fluids does not change much upon mixing. However, in the present case, the ratio depends on the effective radii of the molecules $r_i$ or on $N^\nu$ instead of on the molar volume of the fluids. Equations (11) and (12) imply that by knowing the ratios of the diffusion coefficients in a mixture, the ratios of the radii or chain lengths of the compositions may be determined.

Figure 5:
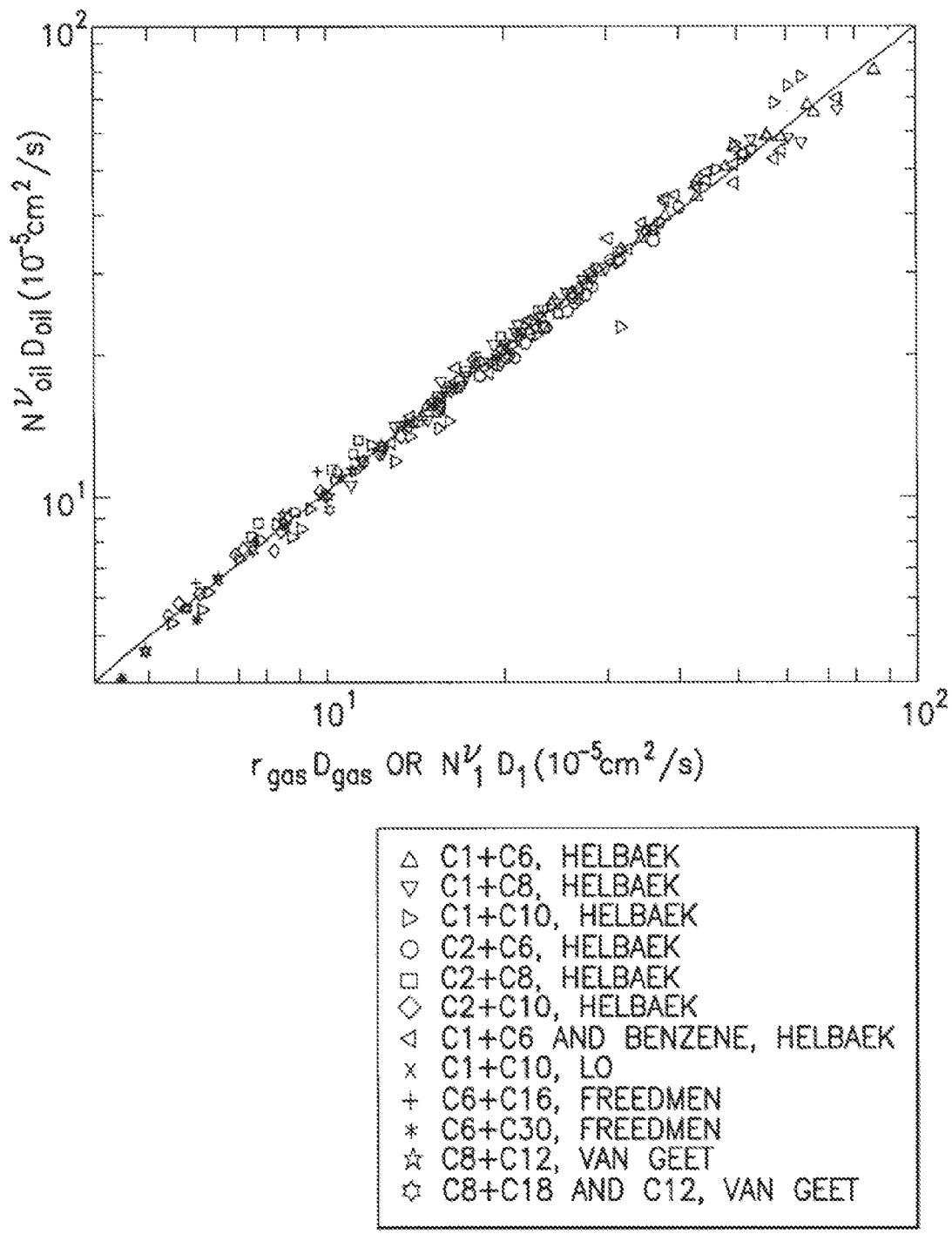
FIG. 5 is a graph demonstrating that $D_i N_i^\nu$ and $D_g r_g$ are constant in binary and ternary mixtures.

Expressing Equations (11) and (12) slightly differently, it is expected that $D_i N_i^\nu$ and $D_i r_i$ are constant for all components within a particular mixture, as shown in FIG. 5. For live oils, the scaled diffusion coefficient of the gas component $D_g r_g$ is plotted along the x-axis. For the dead mixtures, the scaled diffusion coefficient of the lighter oil $D_i N_1^\nu$ is plotted along the x-axis instead. The scaled diffusion coefficient of the heavier oil component is plotted along the y-axis. The theoretical prediction is shown by the black line. The pressures range from atmospheric pressure to 60 MPa and the temperature ranges from 25 to 60° C. The diffusion coefficients are in units of $10^{-5}$ cm$^2$/s. All the points lie very close to the solid line predicted by Equations (11) and (12). With the values of the effective radii and exponent $\nu$ given above (where $\nu=0.7$; see Equations (9) and (10)), the fit works very well both for the live oils and ternary mixtures, in addition to the binary mixtures of liquid alkanes. This fit is noteworthy because the live oils are not ideal fluids. For example, the data on the density of methane and decane mixtures in Lee et al. "Viscosity of Methane-n-Decane Mixtures," J. Chem. Phys. 11(3):281-287 (1966) (incorporated by reference herein in its entirety) clearly shows that the volumes are not strictly additive (i.e., the excess volume is not negligible). Also, some of the mixtures contain benzene or squalene, neither of which are linear. However, they both appear to behave very similarly to what would be expected if they were linear chains. Although the data in FIG. 5 is from the literature, the plot in FIG. 5 represents a new scientific result which explains part of this invention. It shows that the relations in Equations (7) and (8) are valid within mixtures of alkanes (and not just for hard spheres or polymers) over a wide range of temperatures and pressures and determines the values of $\nu$ and $r_i$.

For the alkanes, to a good approximation, the products $D_i N_i^\nu$ and $D_i r_i$ depend only on the mean chain length in the mixture. Thus, $$D_i N_i^\nu = D_i r_i = \frac{ak_B T}{\eta_0} = g(\overline{N}) \quad (13)$$

where $\overline{N}$ is the average chain length in the mixture, given by $$\overline{N} = \sum_i x_i N_i \quad (14)$$

and $x_i$ is the mole fraction of the $i^{th}$ component in the mixture. The function $g(\overline{N})$ also depends on the temperature and pressure. A version of this property, with different values for $\nu$, was originally suggested by Van Geet et al. based on diffusion in mixtures of C8, C12, and C18.

Figure 6:
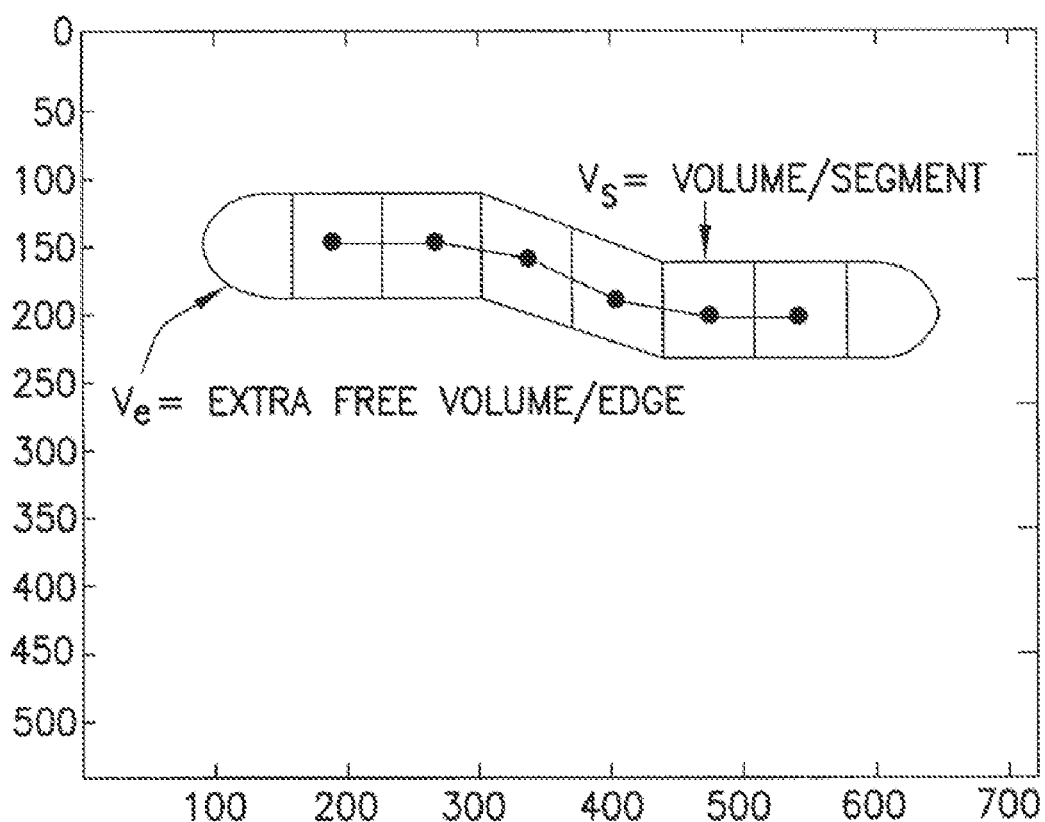
FIG. 6 is a model showing the volume at each segment and the extra free volume at each edge.

The free volume model for alkanes in von Meerwall et al. "Diffusion of Liquid n-Alkanes: Free-Volume and Density Effects," J. Chem. Phys. 108(10):4299-4304 (1998) and von Meerwall et al. "Diffusion in Binary Liquid n-Alkane and Alkane-polyethylene Blends," J. Chem. Phys. 111(2):750-757 (1999) (incorporated by reference herein in their entireties) can be used to give an explanation for this property. In addition to depending on the activation energy $E_a$ for hopping, the probability that segments of the chain will hop depends on whether there is enough free volume available for them to move into. According to this free volume picture, for a pure fluid the function g(N) has the form $$g(N) = A' \exp\left(\frac{-E_a}{RT}\right) \exp\left(\frac{-1}{f(T,M)}\right) \quad (15)$$

where $f(T,M)$ is the free volume fraction, or the volume that is unoccupied divided by the total volume, and M is the molecular weight of the chain. For this application, chain length N and molecular weight M can be used interchangeably (see Equation (29) below) The model in von Meerwall et al. (1998), see FIG. 6, assumes that each segment has fixed amounts of occupied volume and free volume which do not depend on the chain length, but can depend on temperature and pressure. In addition, the increased mobility of each of the two ends in the chain provide additional free volume. (By fitting to data, von Meerwall et al. (1998) show that the extra free volume due to an end is roughly the size of the total volume of a segment.) By a straightforward calculation, with this picture, the density and the fractional free volume for mixtures depend on the chain lengths only through the average chain length $\overline{N}$.

The function $g(\overline{N})$ then depends on the constituents only through the average chain length. Note that the molecular average is used, given by Equation (14) while von Meerwall et al. (1999) instead stipulate that it depends on an average M* defined by $$\frac{1}{M^*} = \sum_i \frac{v_i}{M_i} \quad (16)$$

where $v_i$ is the volume fraction of type i (see von Meerwall et al. (1999)). These two averages are not the same, but in many cases give very similar values, particularly for longer chains.

Figure 7:
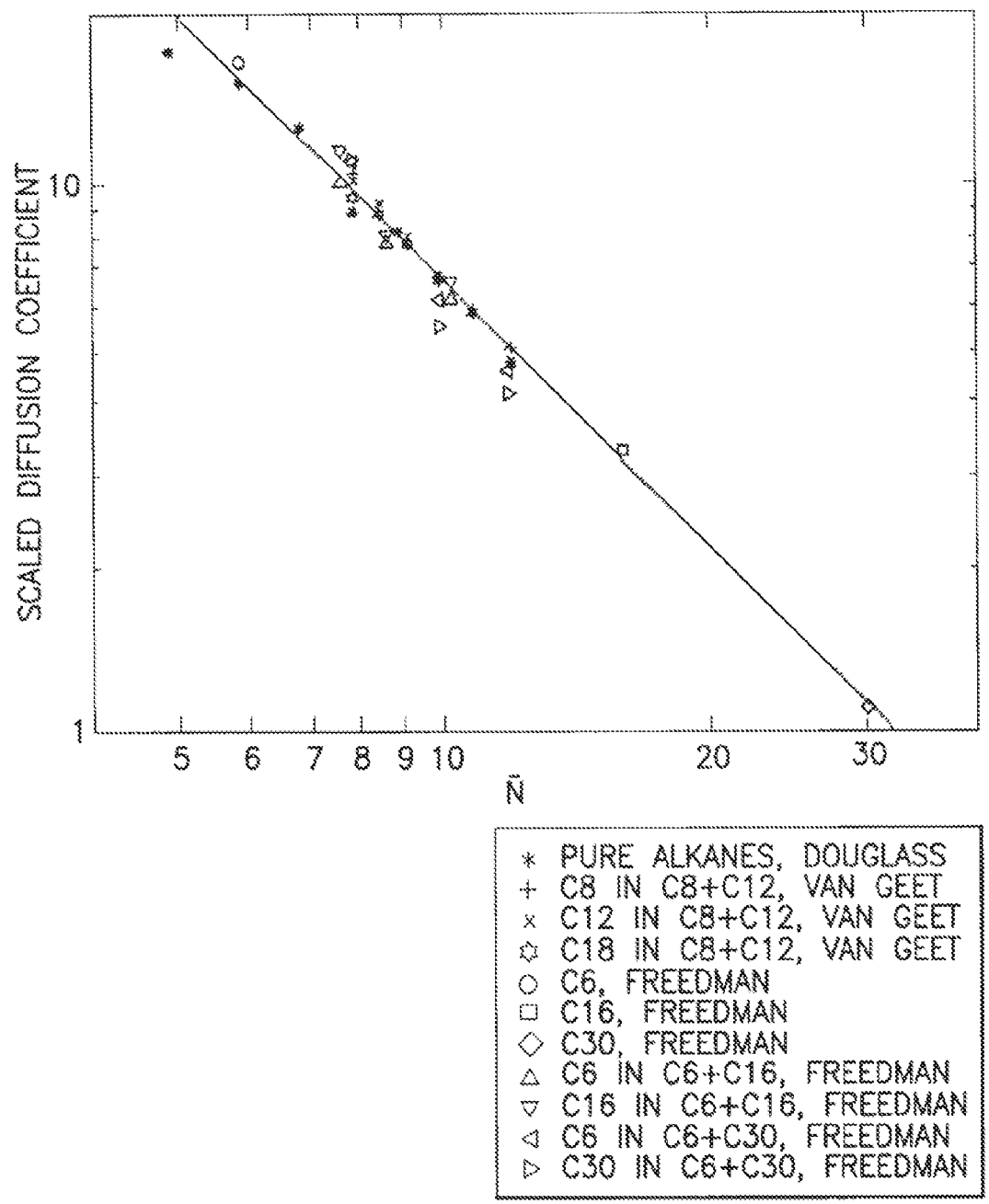
FIG. 7 is a graph depicting scaled diffusion coefficients for pure alkanes and mixtures as a function of mean chain length.

The data for alkanes in Douglas et al. "Diffusion in Paraffin Hydrocarbons," J. Phys. Chem. 62:1102-1107 (1958) (incorporated by reference herein in its entirety) and for mixtures of alkanes in Van Geet et al., Lo et al. (1998), and Freedman et al. appear to fit Equation (13) quite well as shown in FIG. 7. All data is at 25 to 30° C. and at atmospheric pressure. The solid black line shows the fit for the pure alkanes from C6 to C10 and the binary mixtures of C8 to C12 to a power law dependence on the mean chain length.

Figure 8:
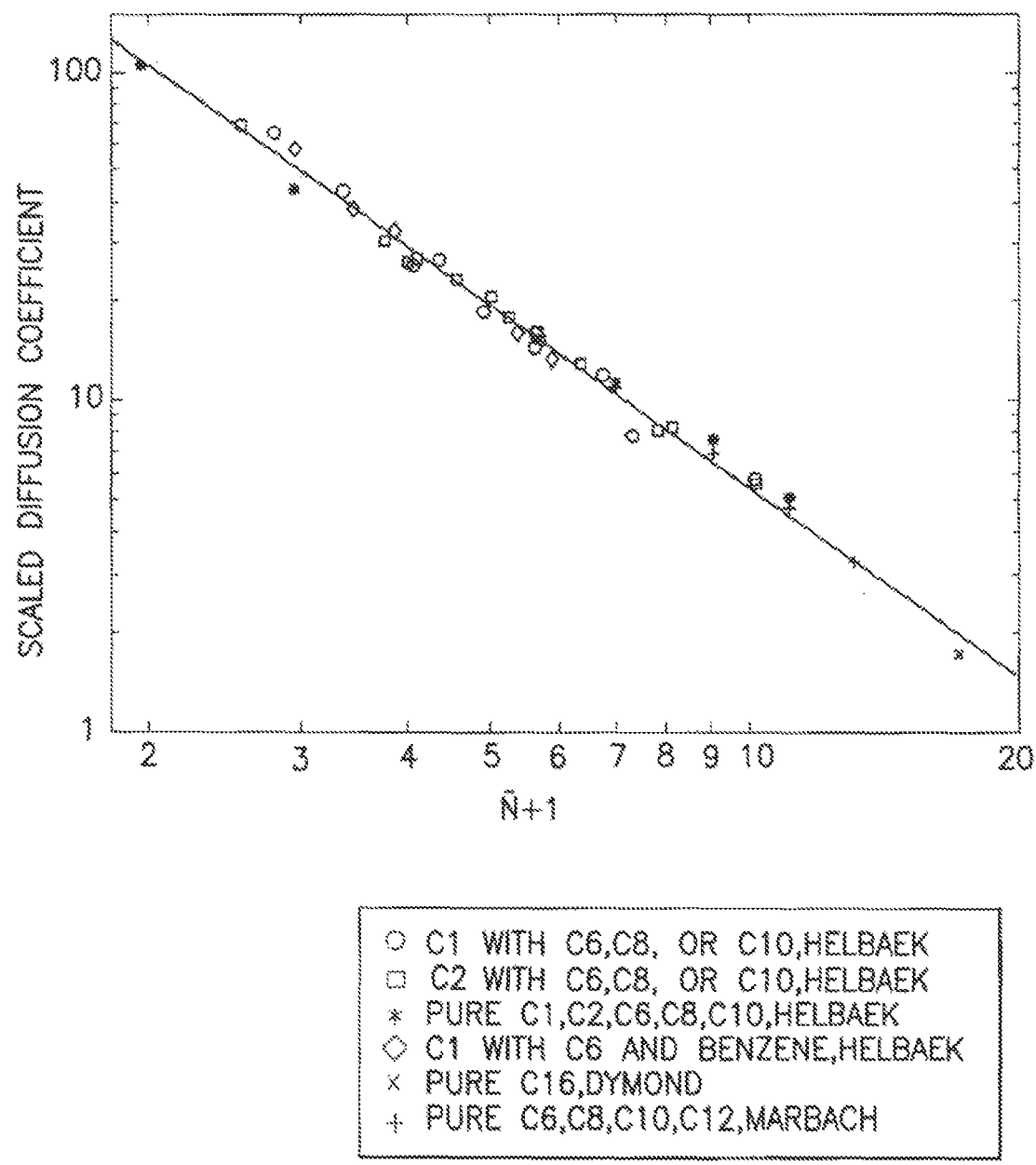
FIG. 8 is a graph depicting the scaling law for live oils.

In addition, for the live oils in Helbaek et al., shown in FIG. 8, the quantities of products $D_0 N_0^v$ and $D_g r_g$ appear to depend only on mean chain length, and even the mixtures with squalene or benzene appear to fit the trend, as shown in FIGS. 7 and 8, respectively. In FIG. 8, the data for live oils from Helbaek et al. is plotted for various temperatures and pressures.

The Scaling Laws The free volume theory gives a complicated functional dependence of $D_i N_i^v$ on $\overline{N}$. However, as originally observed by McCall et al. in "Diffusion in Ethylene Polymers IV," J. Chem. Phys. 30(3):771-773 (1959) (incorporated by reference herein in its entirety) for pure alkanes and polymethylene and further verified by the data for pure alkanes in von Meerwall et al. (1998), the diffusion coefficients can be approximated by a power law over the relevant range of N. According to definition of g(N), this means that g(N) can also be approximated by a power law in N. Thus, because for mixtures g(N) generally depends on mean chain length, it is expected according to aspects of the invention that it will follow a power law with respect to mean chain length, $$g(\overline{N}) = A\overline{N}^{-\beta} \quad (17)$$

where A and $\beta$ are both slowly varying functions of temperature and pressure. The diffusion coefficient for the $i^{th}$ element is then given by $$D_i = A N_i^{-v} \overline{N}^{-\beta} \quad (18)$$

For example, the data for alkanes and mixtures of alkanes (and also mixtures with squalene) at room temperature and atmospheric pressure is plotted in FIG. 7. A and $\beta$ depend on temperature and pressure but not on the constituents. At a temperature equal to 300K and at atmospheric pressure, the line with A=exp(5.6102)×10$^{-5}$ cm$^2$/s and $\beta$=1.6186 is shown in black.

For live oils, $D_i r_i$ still depends on the mean chain length. However, as the chain length nears 1, Equation (18) needs to be modified. The data is still fit well by the function $$D_i = A N_i^{-v} (\overline{N}+1)^{-\beta} \quad (19)$$

Changing $N_i$ to $N_i+1$ will not significantly affect the data with the longer alkanes; however, it will slightly modify the values of A and $\beta$. The data for live oils is plotted in FIG. 8 as a function of $\overline{N}$+1. The fit to Equation (19) for the binary mixtures is shown by the black line in FIG. 8.

Equations 18 and 19 are the scaling laws for the diffusion coefficient that are the basis for this invention. As noted above, scaling laws generally refer to power laws, where one quantity, x, is equal to another quantity, y, raised to some power v, so that x=ay$^v$. Although v is sometimes determined a priori, often v and the constant of proportionality, a, must be determined for the specific properties and conditions of interest.

One aspect of this invention is showing that the diffusion coefficients follow power laws in both the mean chain length of the mixture and the chain length of the particular alkane, as in Equations 18 and 19.

A second aspect of this invention is to give a method for determining the two exponents, v and $\beta$, and the coefficient of proportionality, A, which may depend on temperature and pressure. At a particular pressure and temperature, A and $\beta$ can be determined by several measurements on known fluids or liquids. It is noted that there are different methods for measuring diffusion coefficients including NMR measurements. Because the function $g(\overline{N})$ depends only on the mean chain length, it does not matter which particular alkanes or mixtures are used. In this way, $g(\overline{N})$ may be obtained for the values of temperature and pressure of interest. For example, in FIG. 7, the data for pure alkanes and mixtures of C8 and C12 are fit for A and $\beta$. They are the intercept and slope of the lines in FIG. 7, respectively. As can be seen in FIG. 7, the data for mixtures of C6 and C16 and mixtures of C6 and C30 also fit this line very well. In later sections, it will be shown how to obtain formulae for the temperature and pressure dependence of A and $\beta$.

Another aspect of this invention is that the scaling relation between chain length and diffusion coefficients in Equations (18) and (19) can be used for fluid typing. Typically, in prior art, such as for polymers, only the scaling with the chain length of the component is given. As the composition of the mixture varies, the constant of proportionality will vary. The models in the prior art do not give a method for determining how the constant of proportionality depends on the composition of the mixture, so the chain length distribution of the mixture cannot be determined from the prior art. By including the effect of the other components, via the mean chain length, in the scaling relations of Equations 18 and 19, it becomes possible to solve for the chain lengths from the diffusion measurements. Using Equations (18) or (19) and (14), the mean chain length can be determined from the measured distribution function $\eta(D_i)$ of the diffusion coefficients by $$\overline{N} = A^{\frac{1}{\upsilon+\beta}} \left( \frac{\sum_i f(D_i) * \Delta D_i}{\sum_i f(D_i) D^{1/\upsilon} * \Delta D_i} \right)^{\frac{\upsilon}{\upsilon+\beta}} \quad (20a)$$

Once the mean chain length is determined, the distribution of chain lengths may be determined using $$N_i = \left( \frac{A}{D_i \overline{N}^\beta} \right)^{\frac{1}{\upsilon}} \quad (20b)$$

Any practitioner in the art can see that Equations (20a) and (20b) can be combined by simple mathematical manipulation into a single equation that gives $N_i$ directly in terms of the diffusion distribution. As will be discussed later, the relaxation times also follow a power law of the form of Equation 18 so these same methods noted above can be used for determining chain length distributions from relaxation times.

Figure 1:
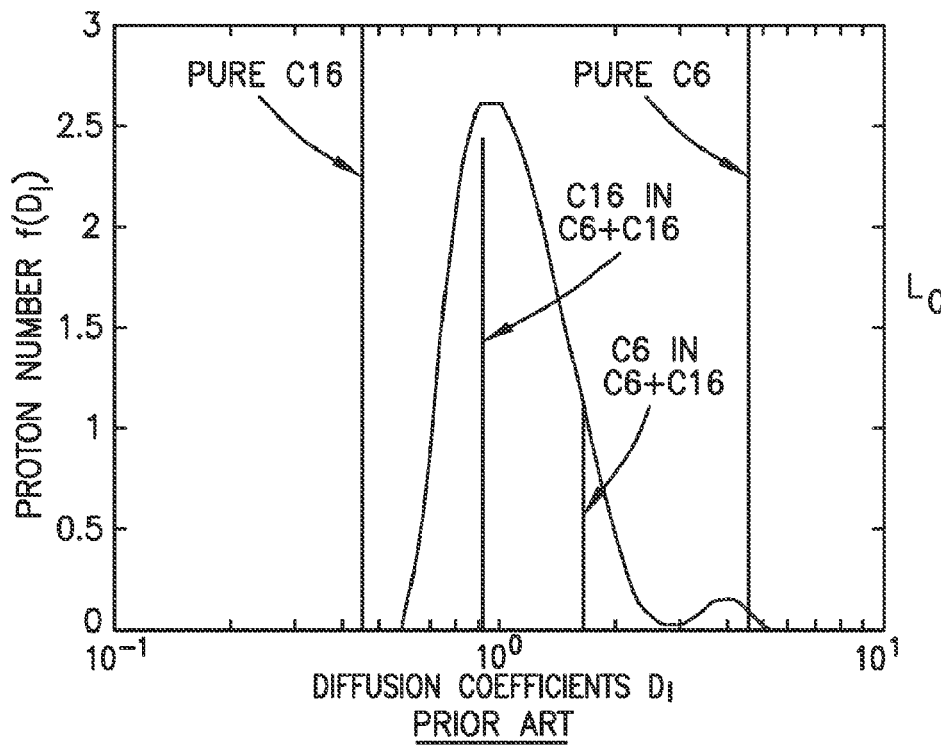
FIG. 1 is a graph showing the relationship between diffusion coefficient (D) and the size of the molecule.

For mixtures of alkanes, the regularized inverse Laplace transform of the NMR data will give a distribution of diffusion coefficients, which can be inverted for the chain length distribution, as described above. One caveat to using the inverse Laplace transform is that it will still give a relatively broad distribution, even in the case where there is only one or two diffusion coefficients, as shown in FIG. 1.

FIGS. 9(a)-(d) show an example where the inversion is applied to two different crude oils, both containing a relatively large amount of saturates, over 85%, so the alkane model may be applicable. The difference between the narrow and broad distributions is clearly reflected in the chain length distributions found by applying the theory from the polymer models to the NMR diffusion data.

Figure 9:
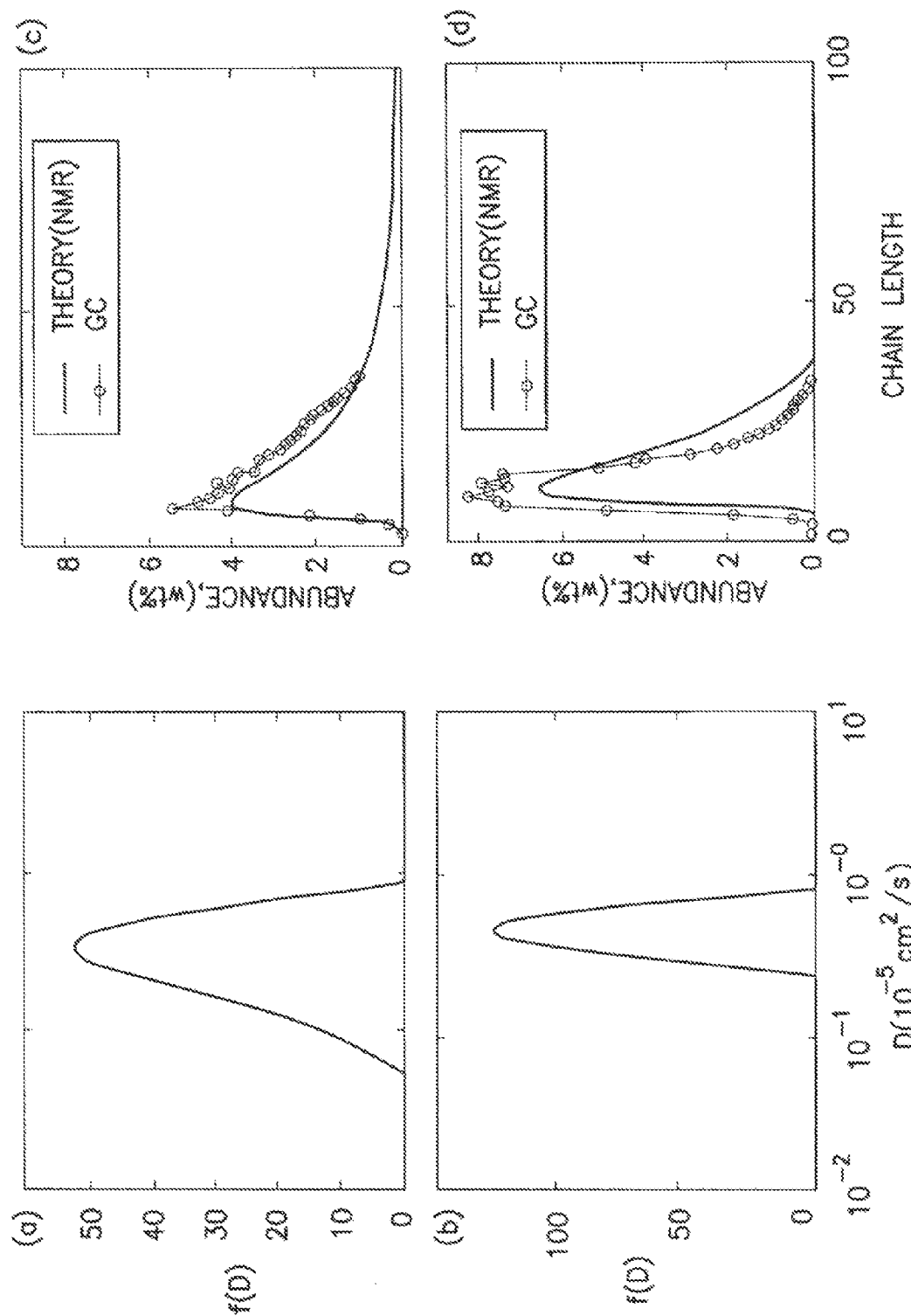
FIGS. 9(a)-(d) are graphs showing chain length distributions for two crude oils.

FIGS. 9(a) and (b) show the diffusion distributions found from NMR data at T=30° C. FIGS. 9(c) and (d) show the chain length distributions. The chain length distribution from the gas chromatography is plotted with the circles ("o") and the chain length distribution found from the distribution of diffusion coefficients and scaling laws is plotted with the heavy black line. Equations (20a) and (20b) were used to calculate this chain length distribution. The values of A and β are the ones found in the fit in FIG. 7).

The polymer model can also be used to find the viscosity of a mixture, given the distribution of diffusion coefficients. For a polymer, according to the Rouse and Zimm models, the viscosity is related to the rotational diffusion coefficient $D_R$ by (see Doi et al. and Ferry)

$$\eta = b' \frac{c}{N} \frac{kT}{D_R} \quad (21)$$

In this equation, c is the number of segments per unit volume and is related to the density ρ by c=ρN/M, where M is the mass of the chain. The constant b' depends on whether the Rouse or Zimm model is used. For both the Rouse and Zimm models without excluded volume effects, the rotational and translational diffusion coefficients are related by $$D_R \propto \frac{D}{Nl^2} \quad (22)$$

Again, the constant of proportionality depends on whether the Rouse or Zimm model is used. Combining equations (21) and (22) gives the relation between the viscosity and the translational diffusion coefficient:

$$\eta = cl^2 bkT/D \quad (23)$$

where b is a constant that depends on which model is used. For the Rouse model it is 1/36 and for the Zimm model it is 0.0833.

Note that the product $\eta D/T$ is independent or nearly independent of chain length (see Lo et al. (2000) and Freedman et al). This would not be the case for hard spheres, where the product would be expected to scale with the chain length. Instead, in the polymer models the chain length scaling drops out due to the "anamolous" dependence on chain length of both diffusion coefficients.

The applicability of these equations for mixtures of short chain molecules and oils, as opposed to polymers, can be checked more quantitatively by comparing the predictions for the values of $\eta D/T$ from the polymer models with those found experimentally. For alkanes and refined oils, $\eta D/T$ was found to be $3.90^{-9}$ cpcm²/sK; for alkanes and crude oils, it was found to be $5.05 \times 10^{-8}$ cpcm²/sK (see Lo et al. (1998) and Freedman et al.). If the density is taken to be ρ≈0.8 g/cm³ and the effective segment length to be l=√6.67×1.54 Å, which is appropriate for long chains (see Flory, *Statistical Mechanics of Chain Molecules*, John Wiley & Sons, Inc., New York (1969), incorporated by reference herein in its entirety), then the Rouse model gives $D\eta/T=2.1\times10^{-8}$ cpcm²/sK. For the lighter alkanes, the Zimm model should be more appropriate. For chain lengths around 10, the effective distance between segments is better given by (Flory) l≈√4×1.54 Å and the density is closer to ρ√0.75 g/cm³, in which case the Zimm model gives $D\eta/T=3.6\times10^{-8}$ cpcm²/sK. A fit to the pure alkanes gives $3.8\times10^{-8}$ which is well within acceptable limits (see FIG. 10).

In a mixture, according to the polymer models (see Ferry), the viscosity is just a sum of the viscosity of each component in the mixture, weighted by the number of molecules of that component per unit volume. Thus, the total viscosity is $$\eta = \sum_i \frac{\text{\# of } i^{th} \text{ molecule}}{\text{unit volume}} \frac{kT}{(D_R)_i} \quad (24)$$

The relation between the translational and rotational diffusion coefficients then gives $$\eta = bckT \sum_i y_i/D_i \qquad (25)$$

where $y_i$ is the weight fraction of the component.

Figure 10:
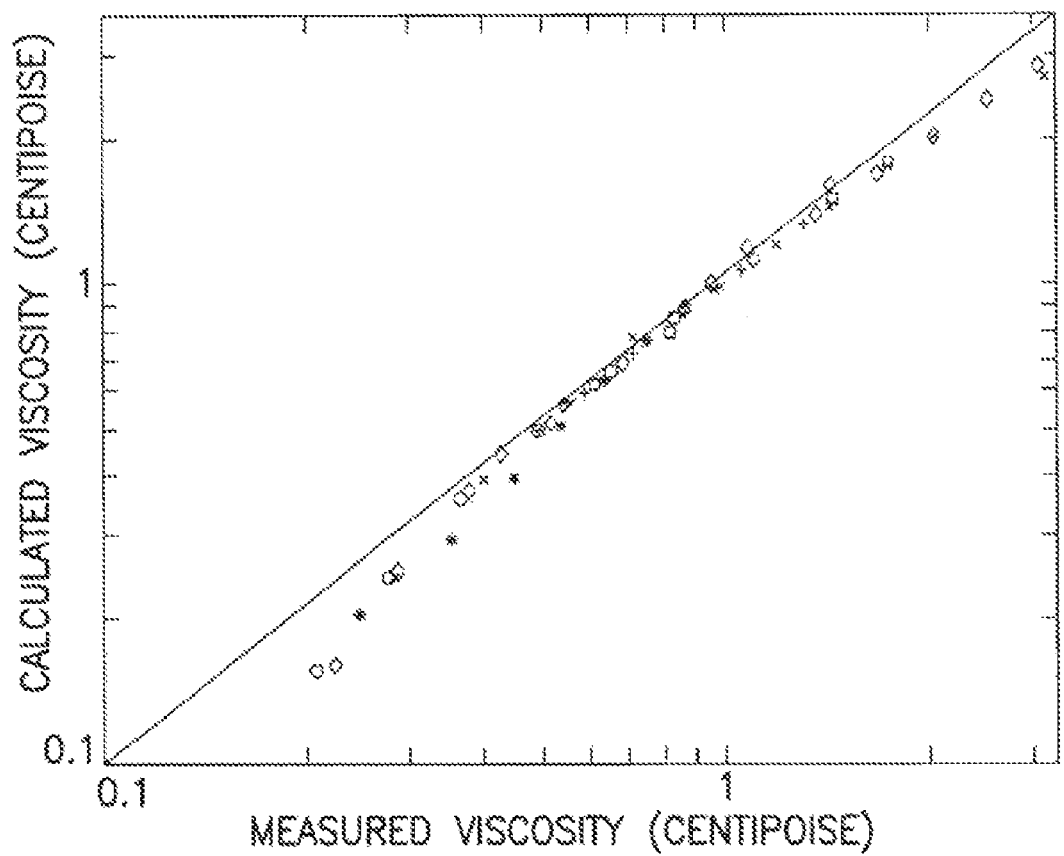
FIG. 10 is a graph showing measured viscosity versus calculated viscosity for pure alkanes.

In FIG. 10, the measured viscosity of mixtures of alkanes is plotted versus the calculated viscosity. Some of the data in this graph is obtained from Rastorguyev et al., *Fluid Mechanics—Soviet Research*, volume 3, page 156 (1974) (incorporated by reference herein in its entirety). They agree remarkably well for such a simple model with no adjustable parameters. Some deviation at the high and low ends of the viscosity range is expected because they are nearing their boiling or freezing point.

Accounting for the Effects of Pressure

It may be preferred that the above model be refined to account for the effects of pressure and temperature on NMR measurements, such as diffusion coefficient and relaxation time. As will be shown below, diffusion coefficient $D_i$ and relaxation times $T_{1,2i}$ are functions of density, instead of depending on both pressure and mean chain length independently. $D_i$ and $T_{1,2i}$ can be determined at elevated pressures if the composition of the oil is known.

As discussed above, the free volume fraction depends on the volume/end $v_e$, the free volume/segment $v_{sf}$, the occupied volume/segment $v_{so}$, and the mean chain length $\overline{N}$. For the purposes of this discussion, it is assumed that the occupied volume does not depend on pressure; only the free volume does. However, for consistency, the same assumption will not be used with respect to temperature dependence (discussed below). This is at least partially justified because temperature changes the intrinsic motion of the molecule, which can affect how much volume it effectively occupies. Once the pressure becomes too high, these assumptions cannot be expected to hold because high pressure may affect the configuration of the molecules, which can in turn affect the occupied volume.

The free volume fraction can be written in terms of the mean chain length and various volumes as follows:

$$f = \frac{\overline{N} v_{sf} + 2v_e}{\overline{N}(v_{so} + v_{sf}) + 2v_e} \qquad (26)$$

Density may also be written in terms of these parameters. For a pure fluid, the density is given by:

$$\rho = \frac{M}{v_T} \qquad (27)$$

where $v_T$ is the total volume/mole and $M = 14.016N + 2.016$ is the molecular mass in grams/mole. For a mixture, the total volume is given by:

$$v_T = \overline{N} v_s + 2v_e \qquad (28)$$

the number of grams/mole is given by:

$$\overline{M} = 14.016\overline{N} + 2.016 \qquad (29)$$

and the expression for the density becomes $$\rho = \frac{14.016\overline{N} + 2.016}{\overline{N} v_s + 2v_e} \qquad (30)$$

Next, in both the expression for the free volume fraction and the density, the pressure and $\overline{N}$-dependent parts may be separated from the rest as follows:

$$f = \frac{[v_{sf}(P) + 2v_e(P)/\overline{N}]}{v_{so} + [v_{sf}(P) + 2v_e(P)/\overline{N}]} \qquad (31)$$

and $$\rho = \frac{14.016 + 2.106/\overline{N}}{v_{so} + v_{sf}(P) + 2v_e(P)/\overline{N}} \approx \frac{14}{v_{so} + v_{sf}(P) + 2v_e(P)/\overline{N}} \qquad (32)$$

Thus, in both the density and the free volume fraction, the only dependence on the pressure and mean chain length is through the combination $$h(\overline{N},P) = v_{sf}(P) + 2v_e(P)/\overline{N} \qquad (33)$$

In other words, the density and free volume fraction may be written as:

$$\rho = \frac{14}{v_{so} + h(\overline{N}, P)} \qquad (34a)$$

$$f = \frac{h(\overline{N}, P)}{v_{so} + h(\overline{N}, P)} \qquad (34b)$$

Then the free volume fraction can be written in terms of the density as follows:

$$f = \frac{14 - v_{so}\rho}{14} \qquad (35)$$

With the assumption that $v_{so}$ is independent of pressure and chain length, all the pressure and chain length dependence of f can instead be replaced by the dependence of $f$ on density. According to Equations (35) and (13) and (15) then, at a fixed temperature, the rescaled diffusion coefficient $D_i N_i^v$ and relaxation times $T_{1i}N_{1i}^k$ and $T_{2i}N_{2i}^k$ should depend only on density, regardless of the mean chain length and pressure. In other words, according to an aspect of the invention, the rescaled diffusion coefficients and relaxation times should be functions only of density and temperature.

Figure 11:
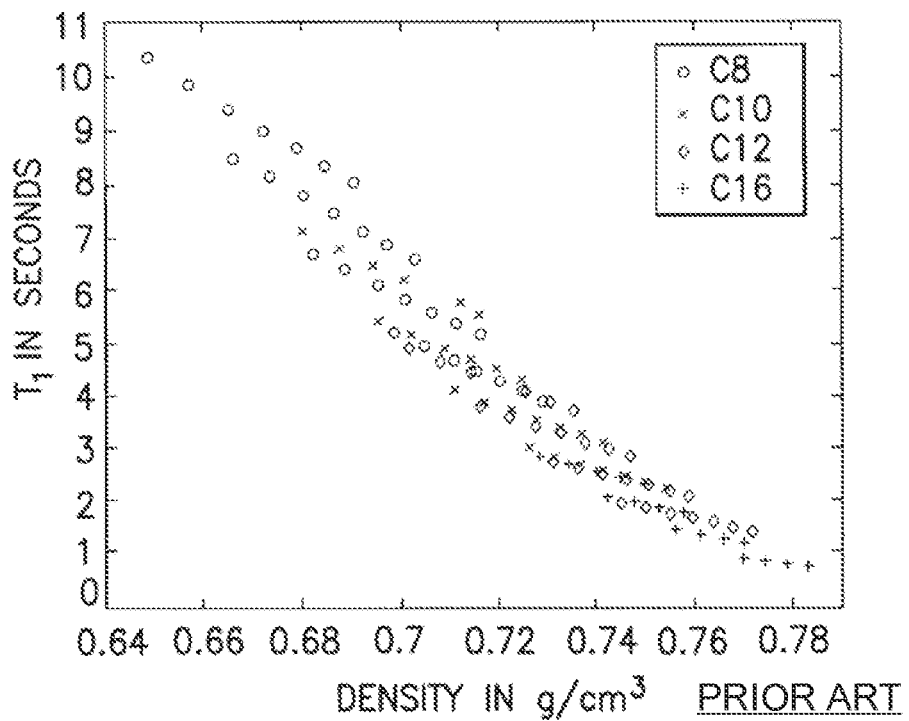
FIG. 11 is a graph showing relaxation times $T_1$ versus density for C8, C10, C12, and C16 at elevated pressures.

In FIG. 11, $T_1$ data for C8, C10, C12, and C16 from Zega's PhD thesis, "Spin Lattice Relaxation in Normal Alkanes at Elevated Pressures", Rice University (1991) (incorporated by reference herein in its entirety) is plotted as a function of density. The temperature ranges from 25° C. to 85° C. For C8 through C12, the pressure ranges from about 20 psia to 600 psia (41 MPa), while for C16, the pressure only goes up to about 400 psia (28 MPa). In this plot, there is no clear connection between the relaxation times of each of the alkanes, except that it increases as the chain gets shorter.

Figure 12:
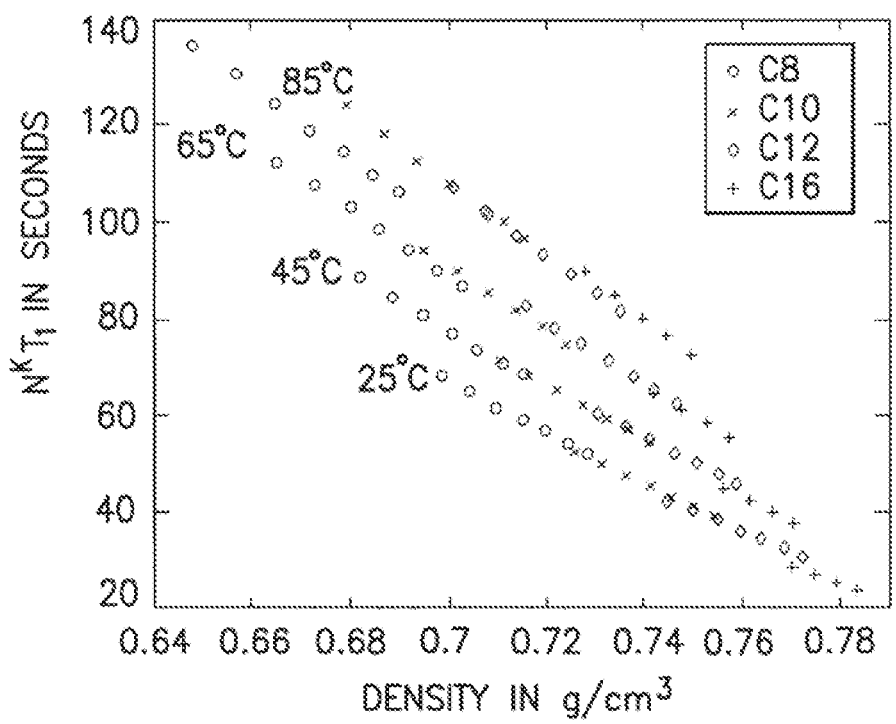
FIG. 12 is a graph showing scaled relaxation times ($N^k T_1$) versus density for C8, C10, C12, and C16.

FIG. 12 shows the scaled relaxation time $N^k T_1 (k=1.24)$ as a function of density. As can be seen in this figure, the data now collapse to four lines, one for each of the four temperatures. The main exception is for octane at a high temperature, and, to a lesser degree, the hexadecane at low temperatures.

Presumably, these discrepancies occur because the octane is getting too close to its boiling point and the hexadecane is getting too close to its melting point, but there could be other explanations for why the range of validity of the collapse is limited. Apart from these limiting cases, the collapse is quite remarkable and demonstrates that for a range of pressures and chain lengths, the scaled relaxation time depends only on temperature and density.

Figure 13:
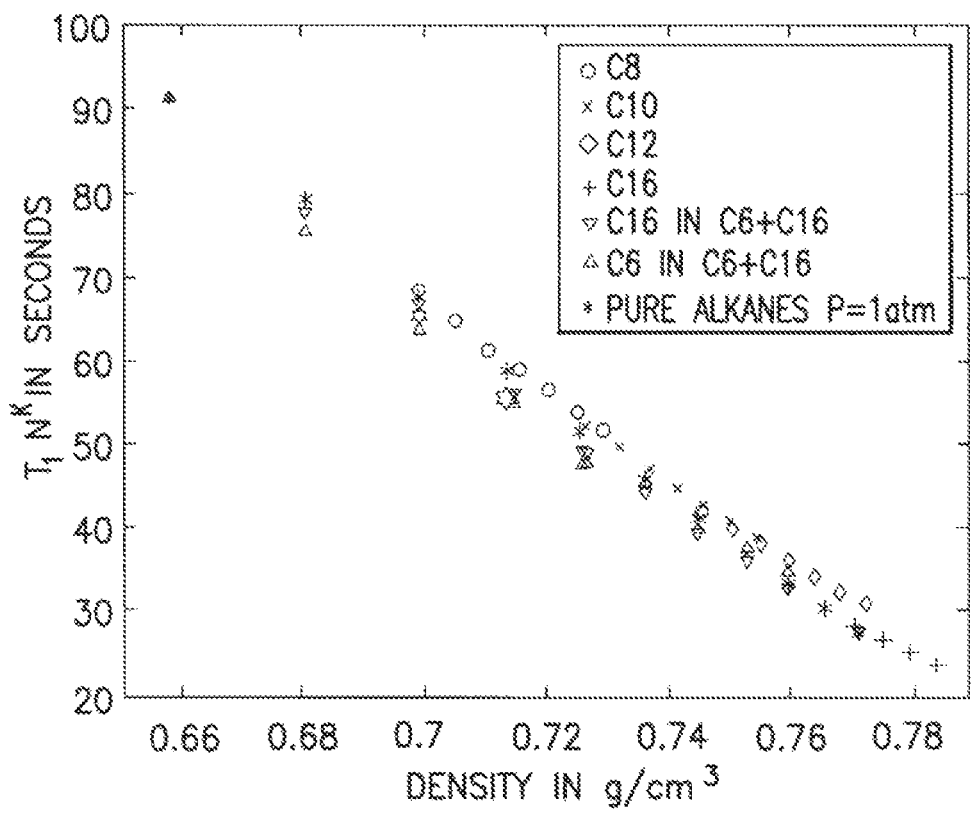
FIG. 13 is a graph showing scaled relaxation times $N_i^k T_{1i}$ versus density for pure alkanes and mixtures at T=25° C.

FIG. 13 shows the data at 25° C. from (1) Zega's PhD thesis, (2) Zega's Master's thesis, "Spin Lattice Relaxation in Pure and Mixed Alkanes and Their Correlation with Thermodynamic and Macroscopic Transport Properties", Rice University (1988) (incorporated by reference herein in its entirety), and (3) Zega, et al., "A Corresponding-States Correlation of Spin Relaxation in Normal Alkanes," *Physics A*, Volume 156, pages 277-293 (1989) (incorporated by reference herein in its entirety). This figure includes data for pure alkanes from C6 to C16 and data for mixtures of C6 and C16 at atmospheric pressure as well as the data at elevated pressure. Again the data collapses to a line, showing that it primarily depends only on density. Also, the agreement between the data for the mixtures and pure alkanes at atmospheric pressure demonstrates that the scaling law within a mixture $T_{1i} \propto N_i^{-k}$, is valid, and that the product $T_{1i} N_i^{-k}$ depends only on the mean chain length. The small systematic discrepancies can be due to the fact that as the chains get closer to hexadecane, they are also getting closer to their melting point. In addition, the scaling law does not really account for intermolecular relaxation, which can vary as the chain lengths vary.

Figure 14:
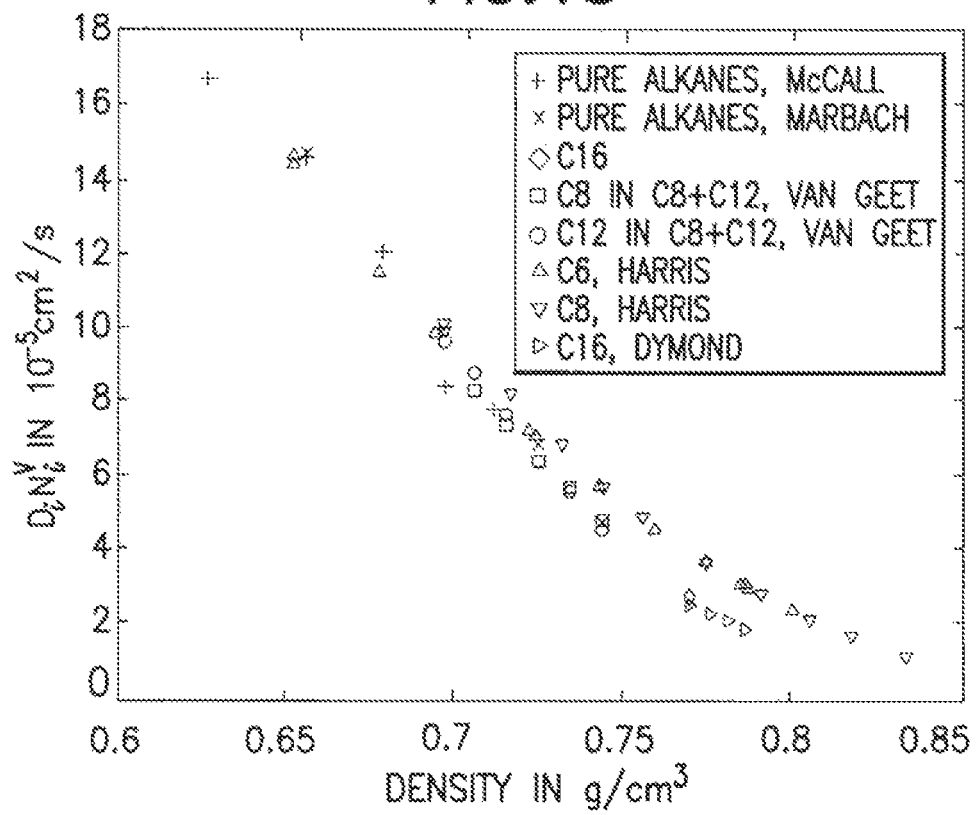
FIG. 14 is a graph of scaled diffusion coefficients $N_i^\nu D_i$ versus density at T=25° C.

Next, the dependence of the diffusion coefficient on density is analyzed. In FIG. 14, the scaled diffusion coefficient $D_i N_i^\nu$ for pure alkanes and some binary mixtures at 25° C. is plotted as a function of density. The data for C6 and C8 from Harris's "Temperature and Density Dependence of Self-Diffusion of n-hexane from 223 to 333 K and up to 400 MPa", *J. Chem. Soc., Faraday Trans*. Volume 1, Issue 78, pages 2265-2274 (1982) (incorporated by reference herein in its entirety) and Harris et al.'s "Temperature and Density Dependence of Self-Diffusion Coefficients of Liquid n-octane and toluene," *Mol. Phys*. Volume 78, Issue 1, pages 235-248 (1993) (incorporated by reference herein in its entirety) range from atmospheric pressure to about 350 MPa. The data for C16 is from Dymond et al.'s "The Temperature and Density Dependence of the Self-Diffusion Coefficient of n-hexadecane," *Mol. Phys*., Volume 75, Issue 2, pages 461-466 (1992) (incorporated by reference herein in its entirety) ranges from atmospheric pressure to 27 MPa. All the other data points are at atmospheric pressure. The equation for density from von Meerwall et al. (1998) was used to obtain the density at atmospheric pressure.

The data collapse reasonably well to a single line. In fact, over the entire range, the agreement between hexane and octane is quite remarkable. However, as the density nears 0.75 g/cm$^3$, the scaled diffusion coefficients for hexane and octane at elevated pressure start to deviate noticeably from the scaled diffusion coefficient for dodecane at atmospheric pressure, and the difference between them and C16 appears to be significant. This deviation occurs at about 250 MPa for C6 and 100 MPa for C8. At these rather high pressures the assumptions about free volume may no longer be valid. In addition, at these high pressures, the equations for the density of hexane and octane may not be valid.

Accordingly, the free volume and, hence, the diffusion coefficients and relaxation times are functions of the density. Accordingly, if the scaling laws are known at the temperature of interest and at one reference pressure, then the relationship between diffusion coefficients and composition can be determined at any pressure, as long as the density of the oil is known. This means that chain length distribution can be determined from a measurement of both density and the diffusion or relaxation distribution.

For the following discussion, it is assumed that the equation for the diffusion coefficient at atmospheric pressure $P_0$ and T is known. If a sample is measured at another pressure P and has density $\rho$ at this pressure, an effective chain length $N_{eff}$ can be defined for the sample as follows. The effective chain length is the chain length that has the same density as the sample, at atmospheric pressure. Thus, $$\rho(N_{eff}, T, P_0) = \rho(\overline{N}, T, P) = \rho \quad (36)$$

Using Equation (30) for density, $$\rho = \frac{M}{N_{eff} v_s + 2v_e} \quad (37)$$

where $M = 14.016 N_{eff} + 2.016$, and $v_s$ and $v_e$ are given by their values at atmospheric pressure. The effective chain length is then given by $$N_{eff} = \frac{2v_e \rho - 2.016}{14.016 - v_s \rho} \quad (38)$$

Equations of von Meerwall et al. (1998) may be used to determine the values of $v_s$ and $v_e$. In von Meerwall et al. (1998), the density at atmospheric pressure is given by $$\rho(T, N, P_0) = [1/\rho_\infty(T) + 2V_E(T)/M]^{-1} \quad (39)$$

where $$1/\rho_\infty(T) = [1.142 + 0.00076T(° C.) \pm 0.005] cm^3/g \quad (40)$$

and $$V_E(T) = [13.93 + 0.060T(° C.) \pm 0.3] cm^3/mol \quad (41)$$

Setting Equation (39) equal to Equation (37) and substituting in the value for the mass M, $v_s$ and $v_e$ may be solved for. The volume/segment is given by $$v_s = 14.016 gmol^{-1}/\rho_\infty(T) \quad (42)$$

and the extra volume/end is given by $$v_e = 2.016 gmol^{-1}/\rho_\infty(T) + 2V_E \quad (43)$$

Next, the diffusion coefficient is calculated at elevated pressure. At temperature T, the scaled diffusion coefficient is a function of density, so that $$N_i^\nu D_i(\rho(N, T, P)) = N_i^\nu D_i(\rho(N_{eff}, T, P_0)) \quad (44)$$

Over some range of temperatures and chain lengths, the diffusion coefficient at atmospheric pressure has the form $$D_i(\rho(N_{eff}, T, P_0)) = A(T, P_0) N_i^{-\nu} N_{eff}^{-\beta(T, P_0)} \quad (45)$$

Above it was shown (see discussion of Equation (18)) that $A(T, P_0) = \exp(5.6102) \times 10^{-5}$ cm$^2$/s and $\beta(T, P_0) = 1.6186$ at 300 K for chain lengths from about C5 to C16; the value for $A(T, P_0)$ and $\beta(T, P_0)$ will be determined for a wide range of temperatures and chain lengths below in the discussion relating to temperature effects. Combining Equations (44) and (45), the diffusion coefficient at pressure P is given by $$D_i(T, P) = A(T, P_0) N_i^{-\nu} N_{eff}^{-\beta(T, P_0)} \quad (46)$$

where $N_{eff}$ is given by Equations (38) through (43).

Figure 15:
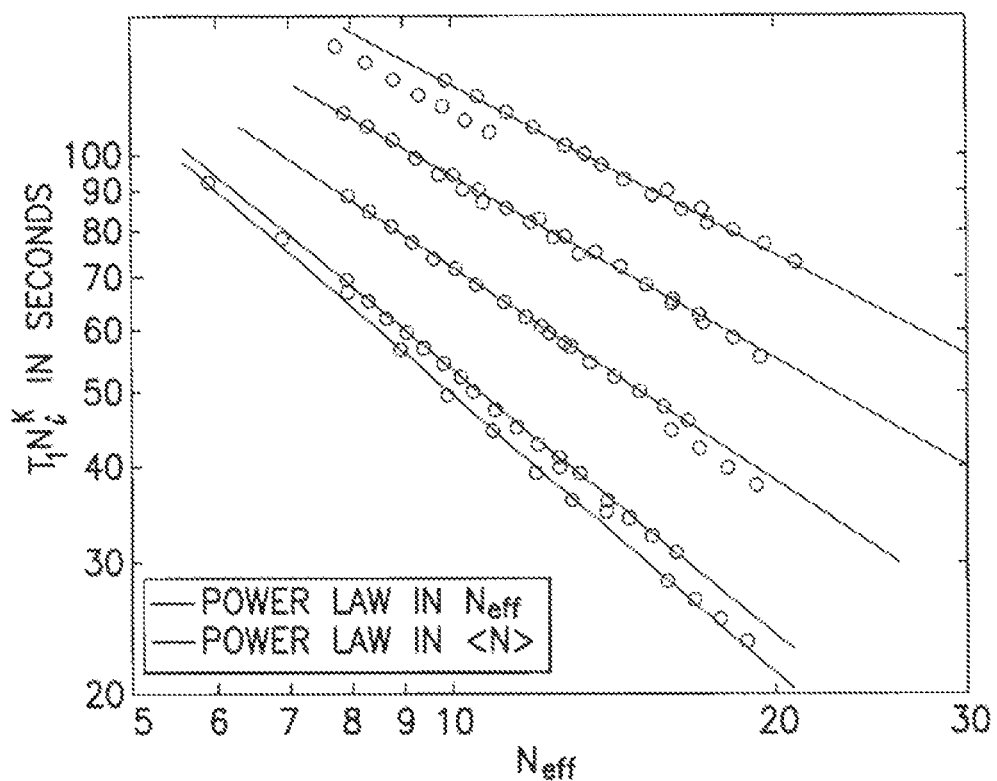
FIG. 15 is a graph of scaled relaxation times $N_i^k T_{1i}$ versus effective chain length $N_{eff}$.

A similar calculation for the relaxation times yields $$T_{1i}(T,P) = T_{2i}(P) = B(T,P_0) N_i^{-k} N_{\mathit{eff}}^{-\gamma(T,P_0)} \quad (47)$$

where $B(T,P_0)$ and $\gamma(T,P_0)$ are the values of B and γ at atmospheric pressure. The version of the scaling laws in Equations (46) and (47) along with the original scaling laws (Equations (18) and (48)) are an aspect of the invention and are the basis for the third embodiment of the invention. To illustrate these equations, in FIG. 15, $T_1$ data from Zega's PhD thesis (see above) is plotted as a function of $N_{\mathit{eff}}$. For each value of T, a separate power law is obtained. The fit for the power laws are shown by the solid lines. At 25° C., a separate fit was performed for the data at elevated pressures A and the data at atmospheric pressure B. The fit at atmospheric pressure demonstrates the scaling law in mean chain length and thus directly validates the original scaling law for $T_1$ given by $$T_{1i} = B(T,P) N_i^{-k} (\overline{N})^{-\gamma(T,P)} \quad (48)$$

This equation is an aspect of the invention. It is the scaling relation for the NMR relaxation times used in all embodiments of the invention. Because it has the same form as the scaling relation for the diffusion coefficients Equation (18), it can be used to determine chain length distributions from relaxation measurements.

For live oils, the reference pressure is preferably not equivalent to the atmospheric pressure for the following reasons: (1) the scaling law is extrapolated beyond the range where it was fit; (2) the scaling law is applied to a regime of short chains which is not truly physical because at atmospheric pressure the alkanes are no longer liquids for chain lengths less than C5; and (3) the linear relationship is used for molar volume versus $N_{\mathit{eff}}(P_0)$ for the short chains, when this relation does not hold. In addition, for the longer chains, getting a 'fit' is ambiguous because it depends on the pressure range of interest.

Figure 16:
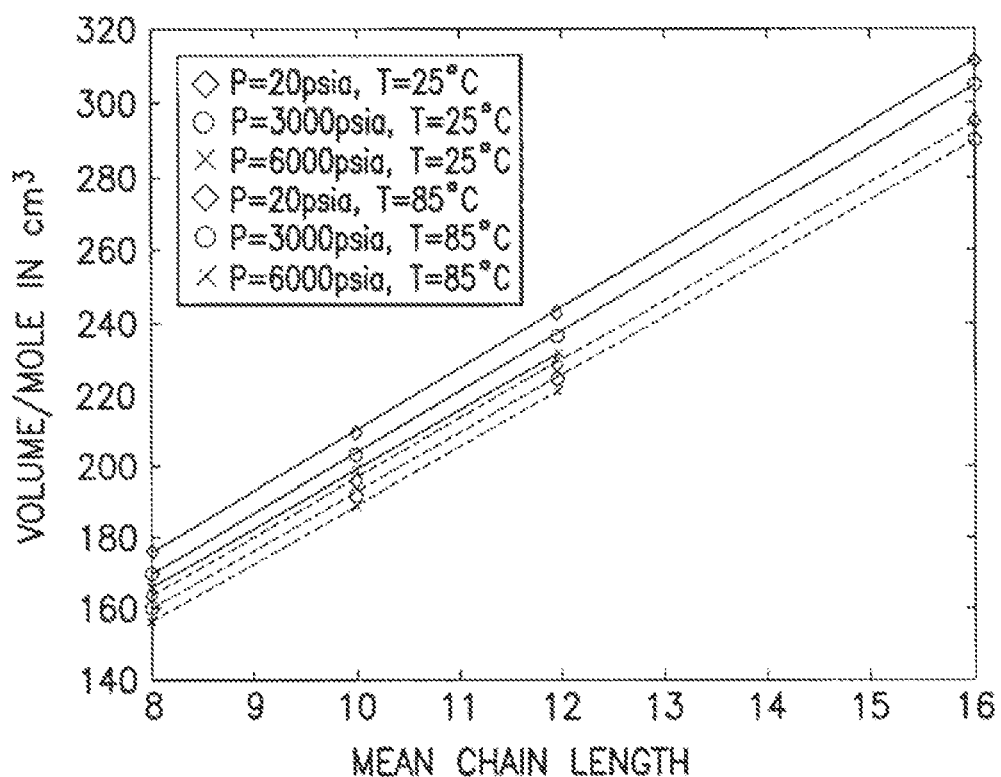
FIG. 16 is a graph of molar volume $v_T$ versus mean chain length $\bar{N}$ using the data of Zega's PhD thesis (see below).
Figure 17:
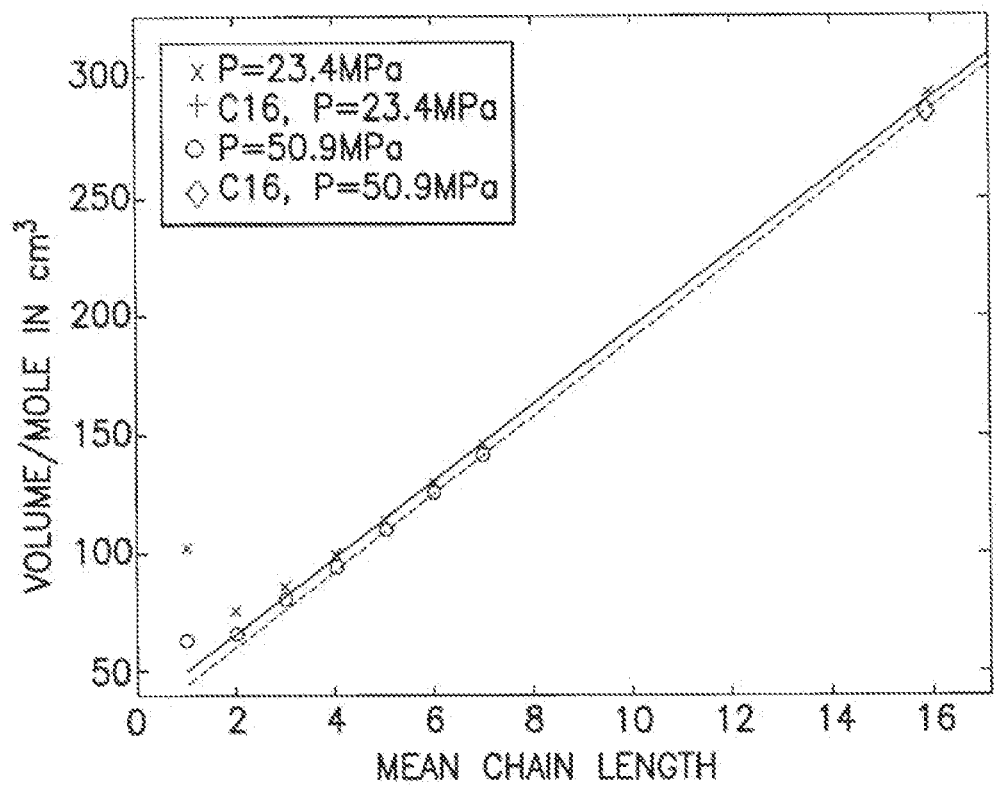
FIG. 17 is a graph of molar volume $v_T$ versus mean chain length $\bar{N}$ for dead and live alkanes at 50° C.
Figure 18:
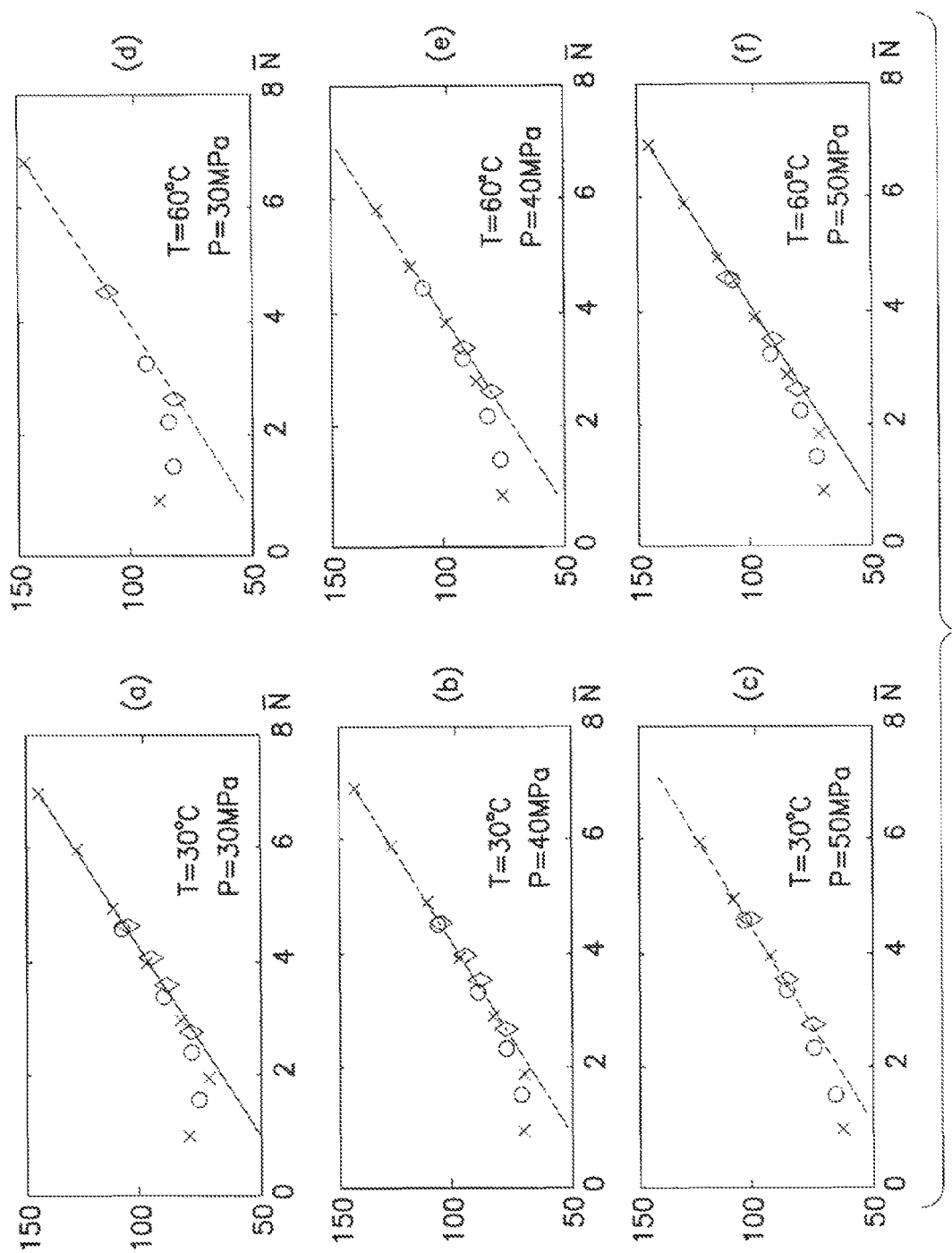
FIGS. 18(a)-(f) are graphs of molar volume $v_T$ versus mean chain length $\bar{N}$ for dead and live pure alkanes and mixtures of alkanes at a variety of pressures and temperatures.

Instead, the scaling law for live oils should be determined using an effective chain length that is defined at an elevated pressure P, where the full range of $N_{\mathit{eff}}(P)$ is covered by the calibration data and where the oil is a liquid or supercritical for the full range of $N_{\mathit{eff}}$. To go from the scaling law in $N_{\mathit{eff}}(P_0)+1$ where $P_0$ is the atmospheric pressure to the plot as a function of $N_{\mathit{eff}}(P_0)+1$ where $P_0$ is an elevated pressure, the density data from the NIST webbook can be used to find the density of all the alkanes up to C7. The data at C6 and C7 is used to find the molar volume as a function of chain length (as shown in FIGS. 16-18). The slope and intercept ($v_s$ and $2v_e$, respectively) are determined using Equation (38). Then the density of the oil sample is substituted into Equation (38) to obtain the effective chain length to obtain $N_{\mathit{eff}}(P_0)$ where $P_0$ is now the elevated pressure.

This method works when $N_{\mathit{eff}}$ is in the physical range of chain lengths or densities and density is not so high or so low that other physics come into play. This method also works primarily when the fluid sample is a mixture of only alkanes because it is very sensitive to the addition of other molecules while D and $T_{1,2}$ are not necessarily affected. Thus, if elevated-pressure mixtures having other molecules in addition to alkanes (such as aromatics and asphaltenes, etc.) are under consideration, a more robust way is needed to take into account pressure effects. The ideas above regarding $N_{\mathit{eff}}$ and free volumes may be applied to a method to calculate the pressure effects that does not require measuring the density of the oil sample. Instead, it only requires knowing the density of alkanes at the pressures and temperatures of interest (plus a reference pressure), which can be found in standard tables such as the NIST webbook. This method is described in more detail below.

First, the pressure dependence of the molar volume will be examined. The molar volume is given by $$v_T = v_s \overline{N} + 2v_e \quad (49)$$

where $v_e$ is the free volume per end and the volume per segment $v_s$ can be broken into the occupied volume per segment $v_{so}$ and the free volume per segment $v_{sf}$. In Kurtz, Jr., "Physical Properties and Hydrocarbon Structure," *Chemistry of Petroleum Hydrocarbons* (Brooks, et al. editors) pages 275-331 (1954) (incorporated by reference herein in its entirety), it was found that $v_e$ varies much more strongly with pressure than $v_s$ does. However, at very high pressures, this difference decreases significantly. The molar volumes $v_e$ and $v_s$ can be determined by looking at density data at a fixed temperature and pressure and plotting the volume $v_T = M/\rho$ as a function of chain length. Several examples are provided in FIGS. 16 through 18(f).

In FIG. 16, the molar volumes calculated from the densities from Zega's PhD Thesis (see above) are plotted as a function of chain length at two different temperatures and three different pressures. As can be seen in the plot, for each temperature and pressure, the data points lie on a straight line. As the temperature and pressure are changed, the intercept changes more than the slope, although the slope does change a little as the temperature is raised.

The values for the slope $v_s$ and intercept $2v_e$ of the fitted lines (shown by the solid lines) are given in Table 1. For comparison, the slope and intercept calculated from Equations (42) and (43) at atmospheric pressure (0.1 MPa) are also given in the table, as well as values at 50 MPa, which are calculated from the data of Lemmon et al., "Thermophysical Properties of Fluid Systems," *NIST Chemistry WebBook, NIST Standard Reference Database Number* 69 (Linstrom et al. editors), March 2003 (http://webbook.nist.gov) (incorporated by reference herein in its entirety) as in the examples below.

| Temperature (° C.) | Pressure (MPa) | Slope $v_s$ (cm³/mol) | Intercept $2v_e$ (cm³/mol) |
|---|---|---|---|
| 25° | 0.1 | 16.27 | 33.20 |
|  | 0.14 | 16.32 | 32.61 |
|  | 20.7 | 16.18 | 30.00 |
|  | 41.4 | 16.01 | 28.45 |
|  | 50.0 | 16.07 | 27.06 |
| 85° | 0.1 | 16.91 | 40.49 |
|  | 0.14 | 16.84 | 40.84 |
|  | 20.7 | 16.74 | 35.56 |
|  | 41.4 | 16.54 | 33.01 |

FIG. 17 is an example of both live and dead alkanes at T=50° C. For N≧3, the fit to a straight line is adequate, and as the pressure is raised, the fit improves for smaller chain lengths. The fits to C6 and C7 extrapolate well to the molar volume for C16. The slope $v_s$ and intercepts $2v_e$ of these lines are provided in Table 2 (below). The data for C1 through C7 is from the NIST webbook, while the data for C16 is from Dymond et al. (see above).

| Temperature (° C.) | Pressure (MPa) | Slope $v_s$ (cm³/mol) | Intercept $2v_e$ (cm³/mol) |
|---|---|---|---|
| 30° | 0.1 | 16.33 | 33.81 |
|  | 30.0 | 16.08 | 30.31 |
|  | 40.0 | 16.09 | 28.79 |
|  | 50.0 | 16.09 | 27.53 |

-continued

| Temperature (° C.) | Pressure (MPa) | Slope $v_s$ (cm³/mol) | Intercept $2v_e$ (cm³/mol) |
|---|---|---|---|
| 50° | 0.1 | 16.54 | 36.24 |
|  | 23.4 | 16.12 | 34.08 |
|  | 50.9 | 16.20 | 29.19 |
| 60° C. | 0.1 | 16.65 | 37.45 |
|  | 30.0 | 16.22 | 33.72 |
|  | 40.0 | 16.25 | 31.74 |
|  | 50.0 | 16.27 | 30.12 |

The densities for live mixtures of C1 with C6 and C2 with C6 are shown in FIGS. 18(*a*)-(*f*). As long as N is greater than about 2 or 3, the volumes for the mixtures are quite close to the interpolated volumes for the pure substances, and they all lie close to the straight lines. FIGS. 18(*a*)-(*f*) show the fits to C6 and C7 and the slope and intercept of these lines are given in Table 2. The data for the pure alkanes was from the NIST webbook, and the data for the mixtures is from Friend, "MST Mixture Property Database," *NIST Standard Reference Database* 14, October 1992 (incorporated by reference herein in its entirety). In Table 2, the values of $v_s$ and $3v_e$ at atmospheric pressure (0.1 MPa) were found using Equations (42) and (43).

In both Table 1 and 2, the slope $v_s$ changes very little as a function of pressure, while the intercept $2v_e$ changes more rapidly. The same trend is true for the temperature dependence. However, both the slope and intercept appear to depend more strongly on temperature than on pressure. Also, $v_s$ and $2v_e$ change more with pressure at higher temperatures than at lower temperatures. The fact that $v_s$ changes so little with pressure supports the assumptions that the occupied volume per segment $v_{so}$ does not depend on pressure.

In order to determine the pressure dependence on the diffusion coefficients, the effective chain length $N_{eff}$ is revisited. A fluid with effective chain length $N_{eff}$ has the same density at the reference pressure $P_0$ as the sample has at its pressure P. For the following discussion, $P_0$ will no longer be restricted to atmospheric pressure. $N_{eff}$ can be written in terms of the mean chain length of the sample as follows, by definition of $N_{eff}$:

$$\rho(N_{eff}, P_0) = \rho(\overline{N}, P) \quad (50)$$

The expression for $\rho$ in Equation (32) is now used to solve for $N_{eff}$:

$$N_{eff} = \frac{2v_e(P_0)}{\overline{N}(v_s(P) - v_s(P_0)) + 2v_e(P)} \overline{N} \quad (51)$$

Based on the values of $v_s$ and $2v_e$ of Tables 1 and 2, the change in $v_s$ with pressure is much smaller than the value of $2v_e$, so, unless $\overline{N}$ gets large (i.e., $\overline{N}(v_s(P)-v_s(P_0))$ is not much smaller than $2v_e(P)$), the first term of the denominator can be dropped to obtain:

$$N_{eff} = \frac{v_e(P_0)\overline{N}}{v_e(P)} \quad (52)$$

Now the diffusion coefficient at pressure P may be determined. As before, $$D_i(\rho(\overline{N}, P)) = D_i(\rho(N_{eff}, P_0)) \quad (53)$$

From the scaling law for $D(N_{eff}, P_0)$, $$D_i(\rho(\overline{N},P)) = A(T,P_0)N_i^{-v}\overline{N}_{eff}^{-\beta(T,P_0)} \quad (54)$$

Substituting in the expression for $N_{eff}$:

$$D_i(\rho(\overline{N}, P)) = A(T, P_0)\left(\frac{v_e(P_0)}{v_e(P)}\right)^{-\beta(T,P_0)} N_i^{-v}\overline{N}^{-\beta(T,P_0)} \quad (55)$$

In this way, the scaling law as a function of $\overline{N}$ for $D_i$ is obtained. The exponent $\beta$ is independent of pressure, so the scaling law has the form $$D_i(\rho(\overline{N}, P)) = A(T, P_0)\left(\frac{v_e(P_0)}{v_e(P)}\right)^{-\beta(T)} N_i^{-v}\overline{N}^{-\beta(T)} \quad (56)$$

The pressure dependence for the relaxation times can be found in a similar way, and has the form $$T_{1,2i}(\rho(\overline{N}, P)) = B(T, P_0)\left(\frac{v_e(P_0)}{v_e(P)}\right)^{-\gamma(T)} N_i^{-k}\overline{N}^{-\gamma(T)} \quad (57)$$

Equations (56) and (57) are an aspect of the invention. They give the pressure dependence of the constants of proportionality, A and B, and the exponents, β and g, which are used in the fifth and sixth embodiments of the invention.

If information about the density of alkanes at the desired temperature T and at both the desired pressure P and the reference pressure $P_0$ is known, then $v_e(P_0)$ and $v_e(P)$, which both depend on T, can be fit. For example, the data in the NIST webbook can be fit to C6 and C7 as in FIGS. 17 and 18(*a*)-(*f*). Then, as long as β(T) and A($P_0$,T) are known, the diffusion coefficient (and similarly the relaxation times) can be determined at any pressure.

Figure 19:
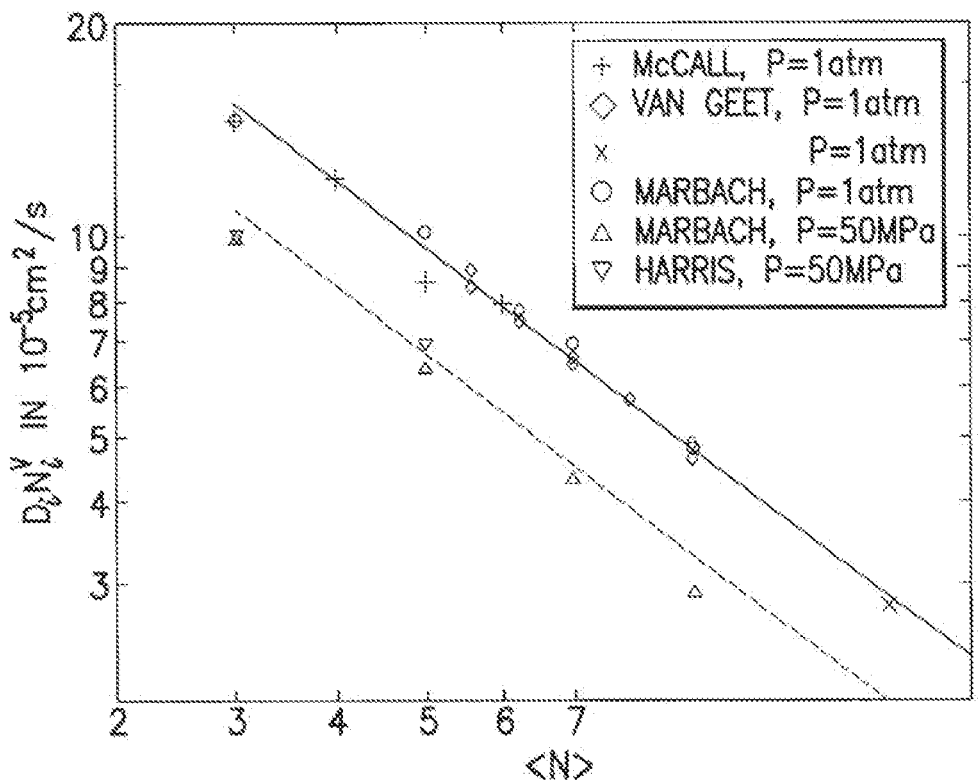
FIG. 19 is a graph of scaled diffusion coefficient $N_i^\nu D_i$ versus mean chain length $\bar{N}$ at 25° C.

An example is provided in FIG. 19, which shows the scaling law at atmospheric pressure and 25° C. The values of $v_e(P_0)$ and $v_e(P)$ with $P_0$=0.1 MPa and P=50 MPa are taken from Table 2. The fit to Equation (56) is shown, where the parameters A($P_0$,T) and β(T) are the values from the scaling law at atmospheric pressure.

Thus, once the scaling law at atmospheric pressure is known as well as some densities at atmospheric pressure and at 50 MPa, a reasonably good fit to the diffusion coefficients at 50 MPa may be obtained with no fitting parameters.

One of the consequences of the pressure-independence of β(T) is that, on a log plot, the curves for diffusion coefficients as a function of temperature or plots of distributions of diffusion coefficients will all lie parallel to each other as the pressure is changed. However, once the pressure becomes very high, the parameter β(T) will have some pressure dependence, as found by Vardag et al., for pressure above about 100 MPa (above about 100 MPa, the slope starts to change). This presumably is an indication that the occupied volume per segment is also affected by pressure at these high pressures. As described below, it is probably also an indication that the diffusion coefficient depends on pressure as well as density at these higher pressures. (This, in turn, should indicate that at high pressures the occupied volume depends on pressure.)

The fact that the exponent β(T) is independent of pressure (at pressures that are not extremely high) follows from the fact that the free volume from the ends is much larger than the change in volume of the segments as the pressure is changed. It also turns out that it is a consequence of requiring the diffusion coefficient D both to depend on pressure and chain length only through density and to follow scaling laws at any pressure. For example, if Equation (51) is substituted into Equation (54) for the effective chain length $N_{eff}$ without imposing any condition on the sizes of $v_s$ and $v_e$, $$D_i(T, P) = A(P_0, T) N_i^{-\nu} \left[ \frac{2v_e(P_0)}{\overline{N}(v_s(P) - v_s(P_0)) + 2v_e(P)} \right]^{-\beta(T,P_0)} \overline{N}^{-\beta(T,P_0)} \quad (58)$$

If $D(\overline{N})$ is required to obey a strict scaling law in $\overline{N}$, the relation in Equation (58) is only possible if the expression in the denominator is replaced with $2v_e(P)$. Thus, the scaling law is only possible if $\overline{N}(v_s(P)-v_s(P_0)) \ll 2v_e(P)$. In that case, the equation of $D_i$ reduces to the scaling law of Equation (56).

For short chains, the molar volume is no longer a linear function of chain length. At the temperatures of FIGS. 21 and 22(a)-(f), this occurs for chain lengths less than or equal to about 2, but as the temperature is raised, it occurs at longer chain lengths. In addition, the scaling law is no longer in $\overline{N}$, but in $\overline{N}+1$. Thus, at pressure P, the diffusion coefficient can be written in terms of the effective chain length at the reference pressure $P_0$ as follows $$D_i(\rho(\overline{N},P)) = A(T,P_0) r_i (N_{eff}(P_0) + 1)^{-\beta(T,P_0)} \quad (59)$$

where $r_i = N_i^\nu$ for the alkanes with chain length larger than about 5, and $r_i$ is proportional to an effective hard sphere radius for smaller chain lengths. If the value of $N_{eff}$ from Equation (52) is substituted into the scaling law for live oils, still assuming that $\overline{N}(v_s(P)-v_s(P_0)) \ll 2v_e(P)$, then $$D_i(\rho(\overline{N}, P)) = A(T, P_0) \left( \frac{v_e(P_0)}{v_e(P)} \right)^{-\beta(T)} r_i \left( \overline{N} + \frac{v_e(P_0)}{v_e(P)} \right)^{-\beta(T)} \quad (60)$$

In all the examples above, the extra free energy from the edges $v_e$ has not changed by more than about 20% as the pressure was varied. It is very useful to have a scaling law in $\overline{N}+1$ for the live oils. Thus, the expression $v_e(P)/v_e(P_0)$ will be replaced with 1 in Equation (60) to obtain a useful expression for the pressure dependence of live oils.

$$D_i(\rho(\overline{N}, P)) \approx A(T, P_0) \left( \frac{v_e(P_0)}{v_e(P)} \right)^{-\beta(T)} r_i (\overline{N} + 1)^{-\beta(T)} \quad (61)$$

The fit to a scaling law does not seem to be that sensitive to this approximation, as will be described below. Equation (61) is a modification of Equation (56), which is used in the fifth and sixth embodiments of the invention when the mean oil is expected to have a significant amount of dissolved gas so the mean chain length is close to one (i.e. roughly less than 3).

Figure 20:
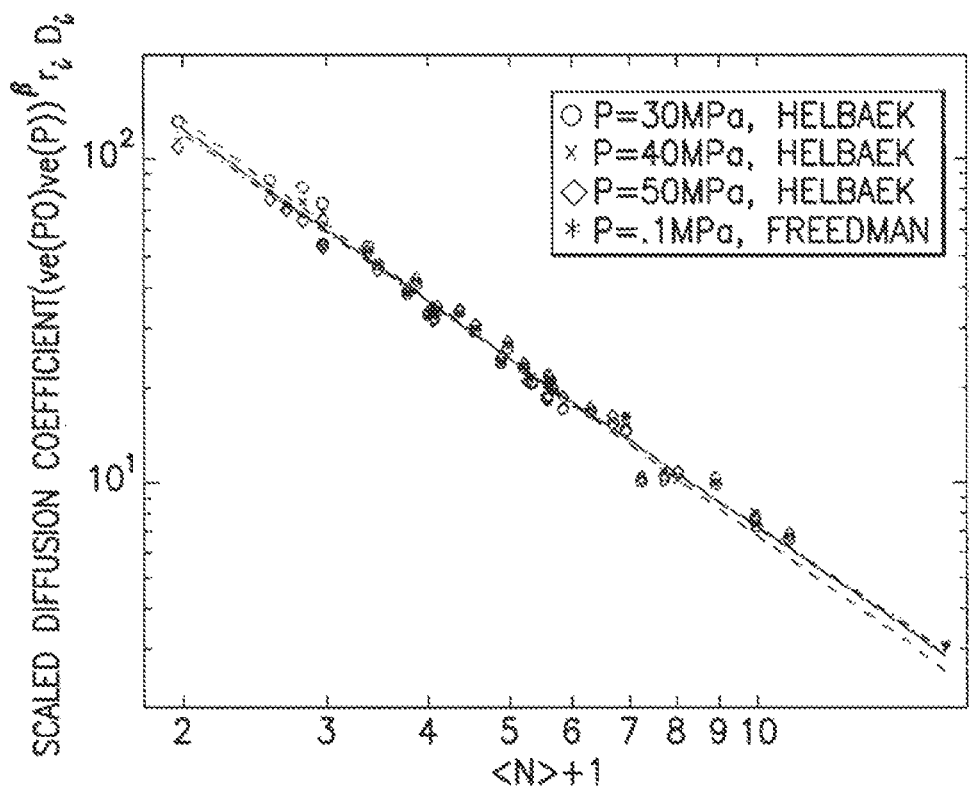
FIG. 20 is a graph of scaled diffusion coefficient $(v_e(P_0)/v_e(P))^\beta r_i D_i$ versus mean chain length+1 ($\bar{N}$+1) for dead and live alkanes at 30° C.
Figure 21:
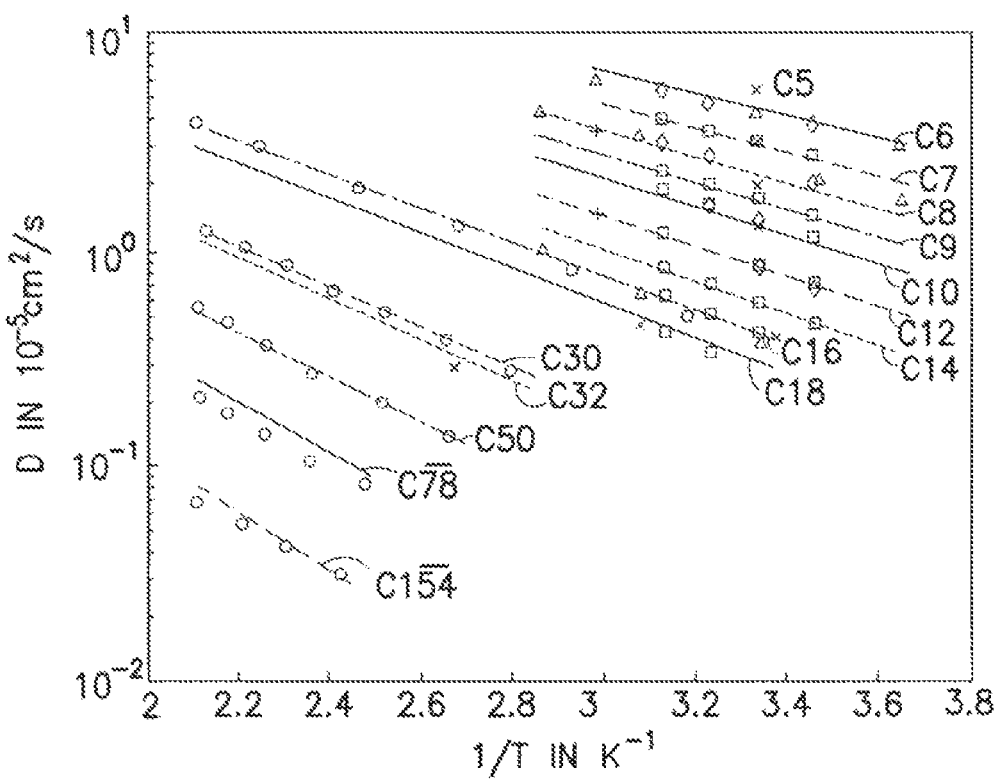
FIG. 21 is a graph of diffusion coefficient D versus reciprocal temperature for pure alkanes at atmospheric pressure.
Figure 22:
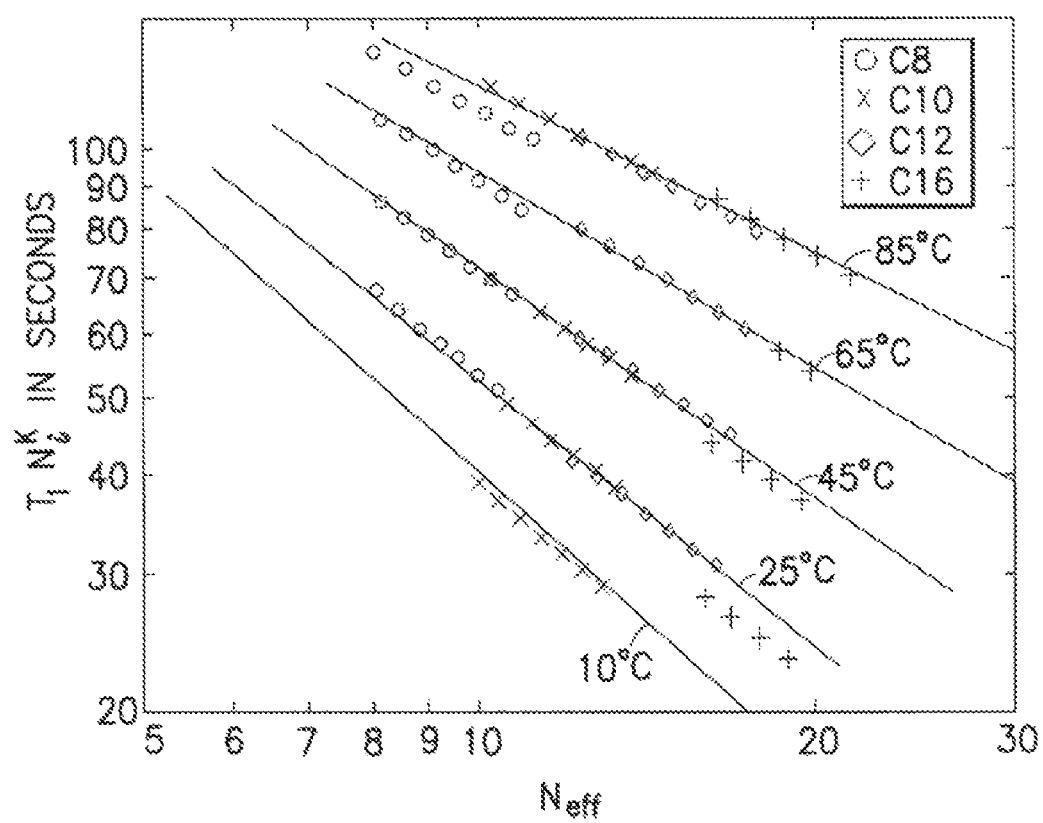
FIG. 22 is a graph of scaled relaxation time $T_1 N^k$ for effective chain length $N_{eff}$.

FIG. 20 shows that the data at different pressures can be collapsed to a single line by using the pressure dependence of Equation (61). In this figure, data from Helbaek is plotted as a function of the mean chain length. The data is at 30 MPa, 40 MPa, and 50 MPa. Data from Freedman et al. is also included at atmospheric pressure (0.1 MPa). Instead of plotting, the usual scaled diffusion coefficient, an additional scale factor of the form $(v_e(P_0)/v_s(P))^{\beta(T,P_0)}$ is included. Thus, $$\left( \frac{v_e(P_0)}{v_e(P)} \right)^{\beta(T)} r_i D_i(\rho(\overline{N}, P)) = A(P_0, T)(\overline{N}+1)^{-\beta(T)} \quad (62)$$

is plotted versus the actual mean chain length of the alkane or mixture. The reference pressure $P_0$ is taken to be atmospheric pressure but the collapse looks very similar if one of the elevated pressures is used instead. The value for $\beta(T)$ used is described below and the values for $v_e(P_0)$ and $v_e(P)$ are given in Table 2 and can be found using the density data from the NIST webbook as described above.

Note that the quantity on the right hand side of Equation (62) depends only on the reference pressure. Thus, the data points at all four pressures should collapse to a single line. As can be seen in FIG. 20, the data collapses very well to a single line, the scatter in the data at a single pressure is much larger than the scatter between data at different pressures. The solid lines show the fits to the scaling law in Equation (19) for the three elevated pressures, which again collapse to a single line. The slope of the line for the lowest pressure (30 MPa) does deviate a little from the two lines at high pressure, and a close inspection of the data points reveals a small systematic tendency for the data at the lowest pressure to have a slightly different slope.

Accordingly, if the scaling law is known at some temperature and reference pressure and if the dependence on chain length of the molar volume is known at the reference pressure and any pressure P, then the diffusion coefficients and the relaxation items may be calculated at pressure P. Having determined the pressure dependence, now the temperature dependence is considered.

Accounting for the Effects of Temperature

The power law dependence on chain length is combined with the Ahrrenius temperature dependence to determine how diffusion and relaxation depend on temperature and chain length. As above, the discussion is focused on diffusion coefficients, but may be similarly applied to relaxation time.

According to Equation (18), the diffusion coefficient follows a scaling law of the form:

$$D_i = A(T,P) N_i^{-\nu} \overline{N}^{-\beta(T)} \quad (63)$$

where $A(T,P)$ and $\beta(T)$ depend on temperature. Alternatively, for pure substances, the diffusion coefficient D has been found to have an Arrhenius temperature dependence of the form $$D \propto e^{-E_a(N)/kT} \quad (64)$$

where the activation energy $E_a(N)$ is a function of chain length (see Vardag et al., von Meerwall et al. (1998), Douglass et al., and Ertl et al., "Self-Diffusion and Viscosity of Some Liquids as a Function of Temperature," *AIChE Journal*, Volume 19, Issue 6, pages 19-40 (1973) (incorporated by reference herein in its entirety)). These two expressions for the diffusion coefficient are consistent if the activation energy is logarithmic in N, of the form $$E_a(N) = b + d \log(N) \quad (65)$$

for some temperature-independent coefficients b and d. This was in fact found in Ertl et al. and von Meerwall et al. (1998). The diffusion coefficient can then be written in terms of four temperature-independent parameters a, b, c, and d in the form $$D_i = e^{-(a+b/T)} N_i^{-\nu} \overline{N}^{-(c+d/T)} \quad (66)$$

In other words, the exponent $\beta(T)$ in the scaling law is given by $$\beta(T) = c + d/T \quad (67)$$

and the coefficient $A(T,P)$ is given by $$A(T,P) = \exp[a(P) + b(P)/T] \quad (68)$$

Because A depends on pressure, the parameters a and b can also depend on pressure. However, since $\beta$ is independent of pressure, c and d should also be independent of pressure. The temperature dependence for the relaxation times can be found in a similar manner, with the result $$T_{1i}=T_{2i}=e^{-(a'(P)+b'(P)/T)}N_i^{-k}\overline{N}^{-(c'+d'/T)} \quad (69)$$

where a'(P), b'(P), c', and d' are temperature-independent parameters. Equations (66) through (69) give the temperature dependence of the coefficients of proportionality, A and B, and the exponents β and γ, which are used in the second, fourth and sixth embodiments of the invention.

To illustrate this temperature dependence, data for diffusion coefficients for pure alkanes taken at a wide range of temperatures and at atmospheric pressure (or saturation vapor pressure) are shown. The diffusion coefficients as a function of reciprocal temperature are plotted in FIG. 21. A four parameter fit was performed for Equations (66) for the diffusion coefficient. All of the data shown in FIG. 26, apart from the data for C8 from Harris et al. and the data for C78 and C154, which are blends of alkanes with mean chain length 78 and 154, respectively, were used in the fit. As can be seen, the data fits quite well to the Arrhenius plots and the lines match up well with the appropriate chain lengths.

The values of the four fitted parameters were
a=−6.3326
b=143.6869
c=−0.2442
d=588.4961 when the coefficient A(T,P) is given in $10^{-5}$ cm$^2$/s. The exponent β(T) varies a fair amount with temperature. At 25° C. it is β(25° C.)=1.73. At 100° C. it is β(100° C.)=1.33, and at 200° C. it is β(200° C.)=1.00. This would appear to be an indication that the occupied volume/segment does depend on temperature. For these temperatures, the coefficient A(T,P) does not vary by as great a percentage, and, in fact, a+b/T is not very sensitive to temperature. For T=25° C., 100° C., 200° C., A(T,P)=347.5×$10^{-5}$ cm$^2$/s, 382.8×$10^{-5}$ cm$^2$/s, and 415.3×$10^{-5}$ cm$^2$/s, respectively.

In order to look at live oils, the data is also fit to Equation (66), with the result
a=−5.7256
b=−212.9887
c=−0.4636
d=705.1817

With these parameters, the fit to the data looks almost identical to the fit with the parameters for the first scaling law. However, as determined above, even though this equation fits the data for the dead oils quite well, it still does not extrapolate well to smaller chain lengths for the live oils.

Next, the $T_1$ data from Zega's PhD thesis is considered. To demonstrate that the data follows an Arrhenius law, the data for C8, C10, C12, and C16 can be plotted at atmospheric pressure versus the reciprocal temperature From the slope and intercepts of the resulting lines, it is possible to find the values of a', b', c', and d'. Instead in FIG. 22, the results of applying a four parameter fit directly to the scaling law in $N_{eff}$ is shown. Accordingly, the parameters have the values
a'=−5.75
b'=−227
c'=−1.43
d'=755 when the $T_1$ is in units of seconds. As with the equation for the diffusion coefficients, these parameters can be used to interpolate for relaxation times at different chain lengths and temperatures. When combined with density data, it can also be used to find the relaxation times at different pressures.

It is noted that while the above applications relate to oil applications, the method may be adapted for other applications including the medical and food preparation industries, for example.

While the invention has been described herein with reference to certain examples and embodiments, it will be evident that various modifications and changes may be made to the embodiments described above without departing from the scope and spirit of the invention as set forth in the claims.

What is claimed is:

1. A method for determining the characteristics of at least one fluid sample under investigation having at least one constituent, wherein the at least one fluid sample includes one of a crude oil, a mixture of homologous hydrocarbon molecules, or some combination thereof, the method comprising:
   a. obtaining measurements of a plurality of calibration samples at a first temperature and a reference pressure, wherein the calibration samples have differing mean chain lengths, and wherein said measurements are selected from the group consisting of one of diffusion coefficients, relaxation times, and combinations thereof;
   b. determining the density of more than one pure alkane or mixtures of alkanes at the first temperature and the reference pressure, wherein density is determined as a function of mean chain length;
   c. determining one of diffusion coefficients, relaxation times or both for the at least one fluid sample under investigation at the first temperature and a second pressure;
   d. determining the density of the at least one fluid sample under investigation at the first temperature and the second pressure;
   e. applying the density function of (b) to the density measurements of (d) and using the measurements of (a) to provide exponents and constants of proportionality so as to determine a first scaling law of diffusion (1), a second scaling law of relaxation (2), or both, at the second pressure in terms of chain length, according to the following:

$$D_i = A(T,P_0)N_i^{-\gamma}\overline{N}_{eff}^{-\beta(T,P_0)} \quad (1),$$

Wherein
   $D_i$ is a diffusion coefficient,
   $N_i$ is the chain length of the $i^{th}$ component,
   $\overline{N}_{eff}$ is the mean chain length of a mixture of one or more alkanes that has the density at the reference pressure ($P_0$) equal to the density of the fluid sample at the second pressure,
   A and β are temperature (T) and pressure (P) dependent coefficients;

$$T_{1i} = B(T,P)N_i^{-k}\overline{N}_{eff}^{-\gamma(T,P_0)} \quad (2),$$

Wherein
   $T_{1i}$ is the spin-spin or spin lattice relaxation time of the $i^{th}$ component,
   $N_i$ is the chain length of the $i^{th}$ component,
   $\overline{N}_{eff}$ is the mean chain length of a mixture of one or more alkanes that has the density at the reference pressure ($P_0$) equal to the density of the fluid sample at the second pressure,
   B and γ are temperature (T) and pressure (P) dependent coefficients;
   f. applying the scaling law of (e) to the data of (c) to determine the composition of the at least one fluid sample under investigation.

2. The method of claim 1, wherein said density measurements of (b) are obtained from standard look-up tables.

3. The method of claim 1, wherein (f) further comprises determining the distribution of chain lengths of the constituents of said at least one fluid sample under investigation.

4. The method of claim 1, wherein the density measurement of (d) is selected from the group consisting of mass density, carbon density, and hydrogen index.

5. The method of claim 1, wherein the at least one fluid sample includes small molecules, the mean length $\overline{N}$ is replaced with ($\overline{N}$+1).

6. The method of claim 1, wherein the at least one fluid sample includes at least one of methane and ethane, the chain length $N_i^v$ corresponding to at least one component being replaced with a molecular radius approximation $r_i$.

7. A method for determining the characteristics of at least one fluid sample under investigation having at least one constituent, wherein the at least one fluid sample includes one of a crude oil, a mixture of homologous hydrocarbon molecules, or some combination thereof, the method comprising:

a. obtaining measurements of a plurality of calibration samples at a reference pressure and at more than one temperature, wherein the calibration samples have differing mean chain lengths, and wherein said measurements are selected from the group consisting of one of diffusion coefficients, relaxation times, and combinations thereof;

b. determining the density of more than one pure alkane or mixtures of alkanes at the reference pressure and at a temperature within or near the range of temperatures in (a), wherein density is determined as a function of mean chain length;

c. determining one of diffusion coefficients, relaxation times or both for the at least one fluid sample under investigation at a second pressure and at a temperature within or near the range of temperatures in (a);

d. determining the density of the at least one fluid sample under investigation at the second pressure and at a temperature within or near the range of temperatures in (a);

e. applying the density function of (b) to the density measurements of (d) and using the measurements of (a) to provide exponents and constants of proportionality so as to determine a first scaling law of diffusion (1), a second scaling law of relaxation (2), or both, at the second pressure in terms of chain length, according to the following:

$$D_i = A(T,P_0) N_i^{-\nu} \overline{N}_{eff}^{-\beta(T,P_0)} \quad (1),$$

Wherein $D_i$ is a diffusion coefficient, $N_i$ is the chain length of the $i^{th}$ component, $\overline{N}_{eff}$ is the mean chain length of a mixture of one or more alkanes that has the density at the reference pressure ($P_0$) equal to the density of the fluid sample at the second pressure, A and β are temperature (T) and pressure (P) dependent coefficients;

$$T_{1i} = B(T,P_0) N_i^{-k} \overline{N}_{eff}^{-\gamma(T,P_0)} \quad (2),$$

Wherein $T_{1i}$ is the spin-spin or spin-lattice relaxation time of the $i^{th}$ component, $N_i$ is the chain length of hte $i^{th}$ component, $\overline{N}_{eff}$ is the main chain length of a mixture of one or more alkanes that has the density at the reference pressure ($P_0$) equal to the density of the fluid sample at the second pressure, B and γ are temperature (T) and pressure (P) dependent coeffecients;

f. applying the scaling law of (e) to the data of (c) to determine the composition of the at least one fluid sample under investigation.

8. The method of claim 7, wherein said density measurements of (b) are obtained from standard look-up tables.

9. The method of claim 7, wherein (f) further comprises determining the distribution of chain lengths of the constituents of said at least one fluid sample under investigation.

10. The method of claim 7, wherein the density measurement of (d) is selected from the group consisting of mass density, carbon density, and hydrogen index.

11. The method of claim 7, wherein the at least one fluid sample includes small molecules, the mean length $\overline{N}$ is replaced with ($\overline{N}$+1).

12. The method of claim 7, wherein the at least one fluid sample includes at least one of methane and ethane, the chain length $N_i^v$ corresponding to at least one component being replaced with a molecular radius approximation $r_i$.

13. A method for determining the characteristics of at least one fluid sample under investigation having at least one constituent, wherein the at least one fluid sample includes one of a crude oil, a mixture of homologous hydrocarbon molecules, or some combination thereof, the method comprising:

a. obtaining measurements of a plurality of calibration samples at a first temperature and a reference pressure, wherein the calibration samples have differing mean chain lengths, and wherein said measurements are selected from the group consisting of one of diffusion coefficients, relaxation times, and combinations thereof;

b. determining one of diffusion coefficients, relaxation times or both for the at least one fluid sample under investigation at the first temperature and a second pressure;

c. determining the relationship of volume of one or more alkanes or mixtures of alkanes to (i) the mean chain length at the first temperature and the reference pressure and (ii) the mean chain length at the first temperature and a second pressure;

d. determining the a first scaling law of diffusion (1), a second scaling law of relaxation (2), or both, as a function of chain length, according to the following:

$$D_i = A(T, v_e(P)) N_i^{-\nu} \overline{N}^{-\beta(T)} \quad (1),$$

Wherein $D_i$ is a diffusion coefficient, $N_i$ and $\overline{N}$ are the chain lengths of the $i^{th}$ component, and the mean length, respectively, β is a temperature (T) dependent coefficient, A is a temperature (T) and molar volume ($v_e(P)$) dependent coefficient;

$$T_{1i} = B(T, v_e(P)) N_i^{-k} \overline{N}^{-\gamma(T)} \quad (2),$$

Wherein $T_{1i}$ is the spin-spin or spin-lattice relaxation time of the $i^{th}$ component, $N_i$ and $\overline{N}$ are the chain length of the $i^{th}$ component, and the mean length respectively, γ is a temperature (T) dependent coefficient, B is a temperature (T) and molar volume ($v_e(P)$) dependent coefficient, using the functions of (c) and the measurements of (a);

e. applying the scaling law of (d) to the measurements of (b) to determine the composition of the at least one fluid sample under investigation.

14. The method of claim 13, wherein the scaling law of (d) is a function of chain length and mean chain length.

15. The method of claim 13, wherein said volume of (c) are obtained using standard look-up tables.

16. The method of claim 13, wherein the volumes of (c) are selected from the group consisting of volume per mole, volume per hydrogen atom, and volume per carbon atom.

17. The method of claim 13, wherein (e) further comprises determining the distribution of chain lengths of the constituents of said at least one fluid sample under investigation.

18. The method of claim 13, wherein the at least one fluid sample includes small molecules, the mean length $\overline{N}$ is replaced with $(\overline{N}+1)$.

19. The method of claim 13, wherein the at least one fluid sample includes at least one of methane and ethane, the chain length $N_i^\nu$ corresponding to at least one component being replaced with a molecular radius approximation $r_i$.

20. A method for determining the characteristics of at least one fluid sample under investigation having at least one constituent, wherein the at least one fluid sample includes one of a crude oil, a mixture of homologous hydrocarbon molecules, or some combination thereof, the method comprising:

a. obtaining measurements of a plurality of calibration samples at more than one temperature and a reference pressure, wherein the calibration samples have differing mean chain lengths, and wherein said measurements are selected from the group consisting of one of diffusion coefficients, relaxation times, and combinations thereof;

b. determining one of diffusion coefficients, relaxation times or both for said at least one fluid sample under investigation at a temperature within or near the range of temperatures of the measurements of (a) and at a second pressure;

c. determining the relationship of volume of one or more alkanes or mixtures of alkanes to (i) the mean chain length at the reference pressure and (ii) the mean chain length at the second pressure;

d. determining a first scaling law of diffusion (1), a second scaling law of relaxation (2), or both, in terms of chain length at the second pressure using the functions of (c) and the measurements of (a), according to the following:

$$D_i = A(T, v_e(P)) N_i^{-\nu} \overline{N}^{-\beta(T)} \quad (1),$$

Wherein
   $D_i$ is a diffusion coefficient,
   $N_i$ and $\overline{N}$ are the chain lengths of the $i^{th}$ component, and the mean length, respectively,
   $\beta$ is a temperature (T) dependent coefficient,
   A is a temperature (T) and molar volume ($v_e(P)$) dependent coefficient;

$$T_{1i} = B(T, v_e(P)) N_i^{-k} \overline{N}^{-\gamma(T)} \quad (2),$$

Wherein
   $T_{1i}$ is the spin-spin or spin-lattice relaxation time of the $i^{th}$ component,
   $N_i$ and $\overline{N}$ are the chain length of the $i^{th}$ component, and the mean length respectively,
   $\gamma$ is a temperature (T) dependent coefficient,
   B is a temperature (T) and molar volume ($v_e(P)$) dependent coefficient;

e. applying the scaling law of (d) with the measurements of (b) to determine the composition of the sample under investigation.

21. The method of claim 20, wherein the scaling law of (d) is a function of chain length and mean chain length.

22. The method of claim 20, wherein said volume functions of (c) are obtained using standard look-up tables.

23. The method of claim 20, wherein the volumes of (c) are selected from the group consisting of volume per mole, volume per hydrogen atom, and volume per carbon atom.

24. The method of claim 20, wherein (e) further comprises determining the distribution of chain lengths of the constituents of said at least one fluid sample under investigation.

25. The method of claim 20, wherein the at least one fluid sample includes small molecules, the mean length $\overline{N}$ is replaced with $(\overline{N}+1)$.

26. The method of claim 20, wherein the at least one fluid sample includes at least one of methane and ethane, the chain length $N_i^\nu$ corresponding to at least one component being replaced with a molecular radius approximation $r_i$.

* * * * *